United States Patent [19]
Wunderman et al.

[11] Patent Number: 6,122,042
[45] Date of Patent: Sep. 19, 2000

[54] DEVICES AND METHODS FOR OPTICALLY IDENTIFYING CHARACTERISTICS OF MATERIAL OBJECTS

[76] Inventors: Irwin Wunderman, 655 Eunice Ave., Mountain View, Calif. 94040-3875; Adolph E. Smith, 602 Moore Creek Rd., Santa Cruz, Calif. 95060-2345; Vijay K. Lumba, 3077 Bates Ct., San Jose, Calif. 95148

[21] Appl. No.: 08/886,561

[22] Filed: Jul. 1, 1997

Related U.S. Application Data

[60] Provisional application No. 60/039,308, Feb. 7, 1997.

[51] Int. Cl.[7] .................................................. G01N 21/00
[52] U.S. Cl. ............................................. 356/73; 356/343
[58] Field of Search ............................... 356/73; 250/343

[56] References Cited

U.S. PATENT DOCUMENTS

| | | | |
|---|---|---|---|
| 5,222,496 | 6/1993 | Clarke et al. | 128/633 |
| 5,239,180 | 8/1993 | Clarke | 250/339 |
| 5,246,004 | 9/1993 | Clarke et al. | 128/633 |
| 5,277,181 | 1/1994 | Mendelson et al. | 128/633 |
| 5,348,003 | 9/1994 | Caro | 128/633 |
| 5,379,764 | 1/1995 | Barnes et al. | 128/633 |
| 5,434,412 | 7/1995 | Sodickson et al. | 250/343 |
| 5,551,422 | 9/1996 | Simonsen et al. | 128/633 |
| 5,565,986 | 10/1996 | Knuttel | 356/346 |

OTHER PUBLICATIONS

I. Wunderman et al., Polarprobe; A Precancer Detection Instrument, Journal of Gynecologic Techniques, vol. 1, No. 2, 1995, pp. 105–109.

I. Wunderman, A Clarification of Spectral Characterization Units for Quantum Detectors and Emitters, Applied Optics, vol. 7, No. 1, Jan. 1968, pp. 25–28.

*Primary Examiner*—Frank G. Font
*Assistant Examiner*—Reginald A. Ratliff
*Attorney, Agent, or Firm*—Lumen Intellectual Property Services

[57] ABSTRACT

An apparatus for photometric analysis and/or identification of properties of a material object comprises a collection of light sources having substantially distinct wavelength envelopes and activated in a rapid sequence of distinct combinations. The apparatus comprises a collection of spatially distributed light detectors which detect radiation from the object and produce detected signals. A signal processor for controlling the light sources and analyzing the detected signals synchronizes the detected signals with the activation of the sequence of distinct combinations of the light sources to produce associated combinations of detected signals which are then analyzed to determine a physical property of the object and/or compared for similarity to previously detected signals from known objects. The photometric data may be combined and correlated with other measured data to enhance identification.

66 Claims, 18 Drawing Sheets

DEVICES AND METHODS FOR OPTICALLY IDENTIFYING CHARACTERISTICS OF MATERIAL OBJECTS

CROSS-REFERENCE TO RELATED APPLICATIONS

The present application claims priority from provisional patent application 60/039,308 filed Feb. 7, 1997, which is incorporated herein by reference. The present application is related to disclosure document No. S00093 deposited Aug. 22, 1995.

FIELD OF THE INVENTION

The present invention relates to identifying and classifying characteristics of turbid, translucent, or mildly opaque materials or objects into predetermined classes, zones or characteristics based on their density of states properties in optical reflection, scattering, transmission, refraction, absorption, phosphorescence and fluorescence from junction emission. The invention constitutes an Identifying Device by Emitter Analysis and the probes are acronymed IDEA probes. In a wide variety of configurations and applications which derive from a relatively few sensing assemblies these devices identify optical properties of an unknown object and into which category it fits.

BACKGROUND OF THE INVENTION

Existing methods which use light to characterize materials generally employ classical spectrophotometric methods. In these methods a spectrally narrow band beam is used together with detectors to quantify the transmission, absorption or reflection of the material. Such a narrow band beam conventionally has a continuously variable wavelength derived by monochromatizing a broadband source. This system functions well, provided that before and after interacting with the material, the transmitted or reflected detection energy is predominantly in the form of a beam. Materials with a high degree of scattering (e.g. biological tissue, colloids, precipitates, polymers) are difficult to accurately quantify in this manner, however, because the radiation loses its directionality after interacting with the material. When a priori predictability of the output radiation pattern is not highly correlated to its input direction, such material will be called turbid in the discussion that follows. Optical dispersion also occurs by angular refractive variations on sample surfaces and is another effect that produces scattering. In these cases, data obtained by conventional methods generally depend highly upon the geometric arrangement. Stability is often poor with low signal to noise ratios because a good deal of the fundamental spectral radiance (photons per $sec/cm^2/steradian/nm$) from the source is wasted in creating a directional beam of which only a small portion is recoverable after interaction. Substantial data processing methods are needed for geometric analysis, noise reduction and stability enhancement.

Spectroradiometers and photometers are most accurate for non-scattering materials. With turbid materials the precise topologic configuration greatly affects the radiation received by a detector. The further the detector is from each point of scattering the more measurement accuracy depends upon geometry. Also, slightly translucent materials having thick dimensions have negligible optical transmission and/or have rough surfaces which scatter light thus preventing accurate measurement of bulk properties. Conventional spectrometers that measure spectral interactions using directional beams poorly accommodate spatial scattering properties of materials.

In the last twenty years techniques have emerged in which the applied wavelengths are not composed of a single spectral peak which can be varied continuously. Instead spectral components can be measured in groups. One such method is known as Hadamard transform spectroscopy and the emitted spectral components are combined in groups based on Hadamard matrices. Such spectral groups are generally applied simultaneously as a beam of radiation and geometric difficulties introduced by scattering are still present. The advantage is that the noise per frequency component can be reduced. The same technique can be applied to images.

A natural system which operates on the global structure of intensities at various frequencies is the eye which has evolved over many millions of years. Animals often receive indefinite visual information from their environment yet some have the ability to perceive very small differences in color. These abilities often exceed the capability of artificial systems so that in the past twenty or so years computer vision workers have turned to study possible analogs in the animal world with the hope of emulating successes of nature. The human visual system has four types of color receptors, the tristimulus red, green, and blue (RGB) cones, and the rods. Yet it is able to distinguish between millions of different colors even when background illumination varies greatly. Spectral aspects of the tristimulus part of this analog to nature has been referenced in U.S. Pat. No. 5,434,412 to Sodickson et al. However, human diversity in color perception, acuity, and ability to recognize through neural data analysis derives in great part from spatial as well as spectral characterization of the retinal image via about 180 million photoreceptors of each eye. Interaction of spectral and spatial photoreception is exemplified by many optical illusions where color changes cause spatial variations and vice versa. The interdependence of spatial and spectral information becomes increasingly significant in materials with increased turbidity. It is also important to recognize that, as a material identifier, color is more than the appearance to the eye in RGB. The identification "colors" of objects extend spectroradiometrically beyond the visible spectrum to all wavelengths. For many materials the most potent optical discrimination properties occur in the infrared region and are invisible to the human eye.

For reasons discussed above, spectroscopic examination of materials for biological analysis, tissue studies, machine vision, industrial control, environmental monitoring, etc. are often hampered by geometric effects of scattering over a broad spectral range. Moreover, spectral density variables employed to analyze materials are often inappropriately applied. Significance of the density of states of the material under analysis, relative to the impinging radiation is often overlooked, as was pointed out by Wunderman in "A clarification of spectral characterization units for quantum detectors and emitters", *Applied Optics,* January 1968.

SUMMARY OF THE INVENTION

This invention attempts to circumvent these difficulties via novel instrumentation means providing a simple spectroscopic material/object identifier that entails a large number of discrete variables in the form of emitter/detector throughputs. The computational power, speed and memory of contemporary computers greatly enhances the feasibility of this spectroscopic identification process for "real time" material/object/property identification.

Classical spectroscopy sorts the radiation source into different wavelength components by means of a monochromator. The output of the monochromator is treated as a "pure" color component of the spectrum. Quantitative meaning has been ascribed to the abscissa and ordinate of plots of such spectral density distributions, with abscissa as wavelength or frequency and ordinate as, for example, watts per unit wavelength or photons per wavelength increment. The ability to readily measure the energy content of a monochromator in watts output (whose output is known to be spectrally narrow) has enabled us to provide what we call "flat" spectral density distributions having constant watts per unit increment. It is often assumed that such a "flat" plot of spectral density defines a unique property which would permit the graphical display of relative response (or sensitivity) as ordinate and wavelength as abscissa when characterizing a material (or radiation).

However if that same "flat" distribution referenced were plotted on an abscissa scale versus frequency (or wavenumber) rather than as wavelength, it would not appear flat unless rescaled and the ordinate were labeled as "watts per wavelength increment" rather than watts per frequency increment which would be inferred when frequency is the abscissa. Moreover, a flat distribution in watts per wavelength increment is not flat in photons per second per unit wavelength. It would also not be flat in a per unit frequency interval. Immediately we see that a spectral distribution is never "dimensionless" (though so often represented) and any ordinate representation depicted as a relative scale is somewhat meaningless unless precisely applicable scale units are expressed for that specific scale. The ordinate always has dimensional units expressed or not, whose units always affect the appearance of the graph. The characteristics of a material investigated using such a spectral distribution would analogously be affected. Units of dimensional scale for the spectral ordinate are an essential variable in characterizing any material, no matter how broad or narrow the radiant distribution is. This immediately leads to the conclusion that the units of any spectral distribution interacting with a material are important and one specific choice may plausibly be preferable to alternate choices. The next logical step is to identify what the impinging radiant distribution interacts with in the material, and to utilize units that are consistent for both radiation and material.

An important concept in understanding the optical response of materials is best understood and analytically quantized in semiconductors, where material imperfections are readily controllable to high precision. The density of states $N(E)$ is defined as the number of quantum states per energy interval $E$ to $E+\Delta E$. $N(E)$ is used in calculating the densities of electrons and holes in a semiconductor. The electron (or hole) densities are given by the product of density of states times the occupational probability that an electron (or hole) is in one of these states. The density of states is a strong analytical function of the dimensionality of the system. With light from a single impinging monochromatic source it is difficult to utilize the density of states of a material for identification purposes. There are generally many levels of energetic transitions that can occur in an object and each single wavelength source excites one transition process at a time. It would require the combination of many separately controlled monochromatic sources impinging on the object at the same time and place to interact with the matrix of possible transitions within the object. This would be extremely cumbersome, inaccurate and hard to control to the required precision. These difficulties are circumvented in the present invention by using a multiplicity of different wavelength semiconductor junction light sources activated individually or in any combination, which can provide the matrix of excitations needed to identify properties of the material associated with its density of states.

In this invention we utilize the optical interaction with a material's density of states as a material identifier. Even in relatively well understood semiconductors the theoretical relationship between density of states and light scattering is quite complex and requires extremely sophisticated methods. This invention circumvents this complexity by using empirical measurement methods that have general applicability to all materials.

Another disadvantage of absorption spectroscopy derived from a monochromatized broad band source is that the applied radiation is only comprised of a narrow wavelength peak at any time. There exists no simple way to rapidly alter the irradiating beam from a single spectral peak to many superimposed arbitrarily different peaks within the broad spectral band covered. Thus it is not feasible to see interaction effects between arbitrarily applied wavelengths and the application of other arbitrary applied wavelengths. The assumption is generally made that such effects do not exist; that there is no interaction among applied wavelengths unless the applied spectral densities become very high. That is, the hypothesis prevails that the material always has a very large density of available states at each applied wavelength compared to the density of excited carriers from impinging photons at energies derived from the applied wavelength. Observed effects are presumed to be linear until the onset of saturation phenomena. However, under careful scrutiny, different wavelength absorptions and emissions from a material are not always totally independent. Fluorescence and phosphorescence are examples where the presence of one wavelength (UV or blue), may influence the detected level of another wavelength, (say yellow). In various minerals and organics the presence of higher energy photons can slightly influence measurements being made at longer wavelengths.

Other examples occur when surface states and trapping levels prevail whose densities are not high relative to impinging interacting photon densities. Different applied wavelengths may not then be linearly independent of other applied wavelengths. The optically excited occupancy of a trapping state in a semiconductor is usually affected not only by photons of energy equal to the gap between the valence band and the trapping level, but also by photons of energy exceeding the bandgap. By consecutively irradiating such material with combinations of wavelengths having all energies (from one to all wavelengths) and monitoring detected signals with an IDEA probe, one is effectively observing the results from a great multiplicity of kinetic rate equations representing transitions within the material. For each irradiation/detection circumstance measured a set of kinetic rate equations would apply within the material which govern the occupancy of all involved excited states and the absorption/emission properties of the material. Elastic scattering would generally be less affected, if at all, unless recoil intervals associated with such scattering approach the intervals between consecutive photon arrivals. This suggests the possibility of using this invention for separately determining scattering and absorption coefficients in a material using the probe device described herein.

In this description the phrase "to associate" is intended to be more general than, and to encompass the phrase "to identify". If, for example, in a group of people wherein on John Doe has a twin brother Joe Doe outside the group, associating Joe with members of the group into an ordered hierarchy would find Joe as identified with John. But, association as used herein also implies the capacity to sort the order of identifications of Joe with all other members of the group. Thus this invention's ability to sort, classify, denominate, categorize, systematize, rank, the quantitative interrelationship of group members as well as user defined divisions, like families, genus, species, kind, type, variety, fashion, mannor, mode, style, etc., is deemed to be an important improvement over that prior art which merely identifies materials by their properties. Notwithstanding that intended distinction of this invention, the specification uses the words "associate" and "identify" interchangably for reasons of reader familiarity.

The present invention comprises an optical characterization and inspection method to identify properties or characteristics of an object as belonging to a predetermined class. A preferred embodiment of the invention comprises (1) light sources comprising a multiplicity of LEDs prearranged in spatial positions and fixed or moveable relative to the object and having a controlled lighting sequence that is predetermined or computer controlled, (2) detection means having a plurality of discrete detectors such as silicon, germanium, lead salts, etc. sensitive to the LED wavelengths. In another embodiment the detection means may consist of a charge coupled device (CCD), a charge injection device (CID), camera, an image intensifier, CMOS imaging chip, photoconductor detectors, avalanche detectors or photomulitpliers.

(3) a signal processor for receiving the detected signals and algorithmically compare those signals with signals from other referenced objects, discriminating and sorting degrees of association between properties of the objects.

DETAILED DESCRIPTION OF THE INVENTION

Figure 1A:
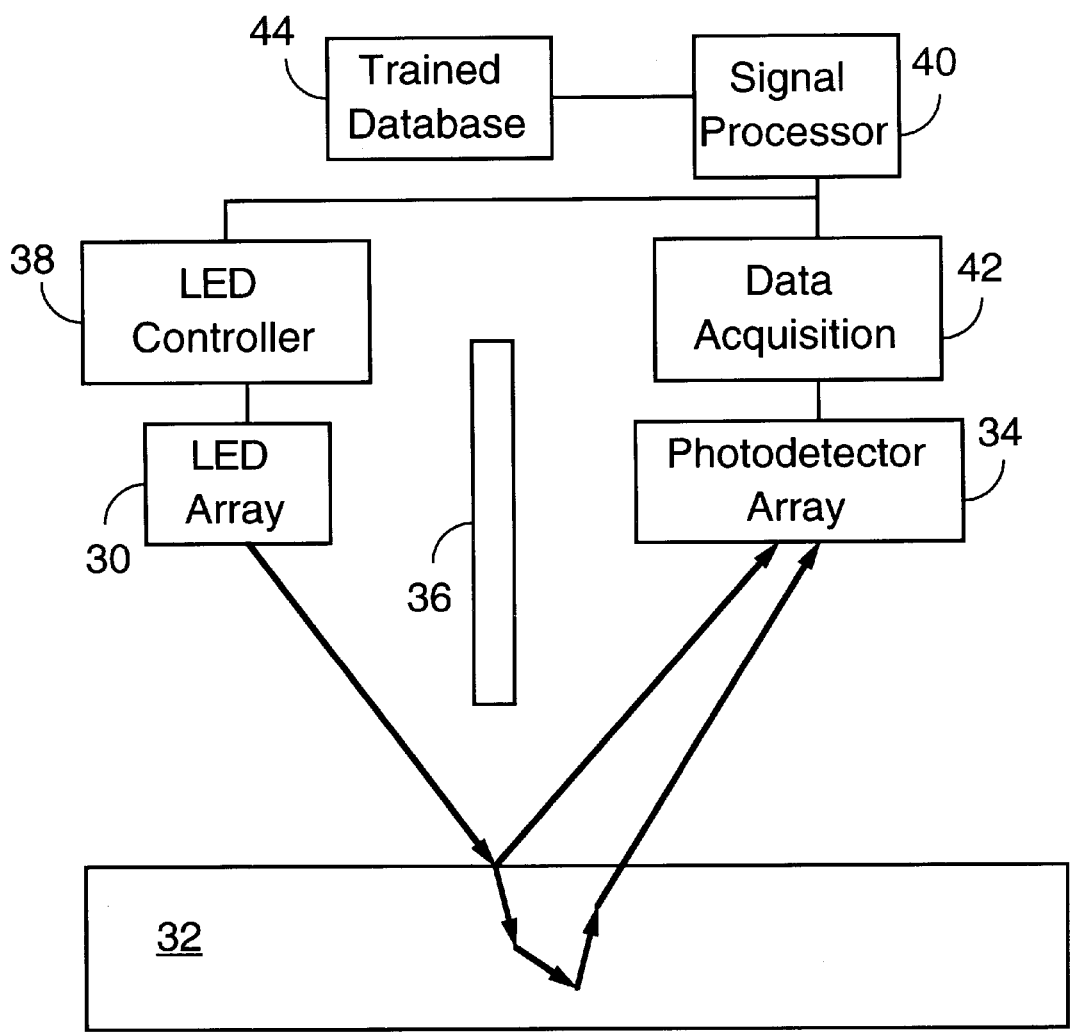
FIG. 1A is a block diagram of a preferred embodiment of the invention wherein the optical barrier is at a distance from the object surface.

The present invention provides a means for optically identifying properties of a material, or determining a degree of similarity between materials, whether the material is opaque, turbid or transparent in a selected band of the electromagnetic spectrum, preferably 400 nm to 5,000 nm. By using relatively inexpensive LEDs and photodetectors it is possible to perform analyses and identifications which were previously done with much more expensive apparatus. In some circumstances, there was virtually no existing other method to perform comparable analyses. As will be described below, in a preferred embodiment the LEDs employed are in the form of semiconductor die, each of about 0.03 cubic mm in volume. Thus the entire configuration can be exceedingly small compared to conventional spectrometers. Spectral radiance at the LED surface and in close proximity can be comparable to that of a several hundred watt quartz lamp at significantly less supply current, voltage and size. Output from the die does not have to pass through a monochromator and a multiplicity of different wavelength die can be placed very close to the test sample. Photon output in each energy interval (E to E+$\Delta$E) is ostensibly linear with drive current and thus compatible with the analysis in photon densities and density of available states within the material. Also, LEDs can be switched on and off in microseconds or less. Other radiation sources currently utilized in spectrometers do not have these features.

It is noted that the primary distinction between an LED which functions via junction luminescence and a diode laser which functions via junction luminescence is the optical cavity configuration of the junction die. Accordingly, this invention also encompasses utilization of diode lasers as sources constituting one configuration of junction luminescence illuminators. Polymer luminescent LEDs can also be used as alternatives to single crystal junction LEDs. Accordingly, the term LED is used in the present description to mean any semiconductor device wherein excited carriers generated in a region can radiatively recombine and thereby emit photons. Historically in fact an earliest published acronym for LEDs and diode lasers was ILD (Injection Luminescent Diode). They include conventional III–V, and II–VI LEDs, diode lasers and polymer luminescent emitters. These processes can usually be depicted as those in which electrons may be excited by several alternative means into excited states and recombine via transitions into unoccupied states. Alternative means by which the electrons may be excited are injection via cathode luminescence or photoluminescence or avalanche breakdown in reverse biased junctions. The term "scattering" is used in the present description to include any photon absorption/re-emission processes such as resonance fluorescence, Stokes or anti-Stokes fluorescence, phosphorescence, and photoluminescence. Certain LED types, while they are not emitting in the forward bias mode, can be time-share-switched for employment as narrow spectral band photon-to-electron detectors to help discern different types of absorption/re-emission processes occurring in the test sample.

The LEDs described herein can be driven on and off by either multiplexers, analog switches, hex fets, junction transistors or any suitable devices which can provide adequate current at sufficiently rapid intervals. In some instances, rather than employing off-on switching to a predefined current level, a modulation frequency is applied to each on-LED and the relative amplitude and/or phase of the detected signal at that frequency is also used as a discriminant. This can be useful in cases where the test sample exhibits measurable temporal properties under phosphorescence, fluorescence, thermal property shifts or other reactions induced by the radiant illumination which associate with scattering, transmission time, or lifetime delays. Standard electronic methods to establish amplitude and relative phase of the detected signal frequency are employed. Higher energy LEDs are generally used for excitation where fluorescence and phosphorescence are present and a filter or colored dye which selectively blocks specific wavelengths cover at least some of the detectors. Thus the applicable types of LED excitation can be continuous (DC), pulsed, amplitude modulation (AM), frequency modulation (FM), phase modulation (PM), spread spectrum, or specific waveform functions like a triangular ramp wave can modulate amplitude or frequency. Just as various sources can be used, the analogous condition exists for the detector array which could be discrete, assembled, or integrated arrays of cooled or uncooled PIN, planar, avalanche, photovoltaic, photoconductive photodiodes, phototransistors as well as linear, circular and XY-CCD arrays, image intensifiers, photomultipliers, thermopiles, and a wide variety of polycrystalline detectors.

Photons comprising the impinging spectral distribution interact with the density of available states within the material. For example to establish the degree of absorption, one should multiply the density of available absorption states within the material in an energy interval (E to E+ΔE) by the number of impinging photons per second in the energy interval. Similarly, for elastic scattering, the photons/sec in a momentum interval P to P+ΔP interact with the density of available momentum states in that momentum interval. Elastic scattering states may often be associated with a directional, anisotropic parameter. [Classical scattering states associated with the density of energy states is also feasible.] Multiplications that employ two different sets of units like (states within an energy interval)×(photons within a wavelength interval) are ad hoc and nonsensical. Recognizing that what is being optically characterized is the material's density of available states in relation to the impinging radiation establishes the relevant units in which the radiation should be quantified. The transmitted, absorbed, reflected or scattered radiation that can be detected in proximity of the test material is the consequence of the test material's density of available states for each spectral frequency interval applied and detected in each direction. The sum total information matrix of how radiation impinging on the material emitted from a multiplicity of different spatial positions (each with a respective frequency) is detected by a second multiplicity of detectors in proximity, is the matrix which characterizes the density of states of the material for those frequencies and geometry.

For reasons of simplicity a discussion of the invention in terms of density of states is provided in general terms. Those skilled in the art will appreciate that the following discussion applies to all the specific embodiments which follow.

A block diagram of a preferred embodiment of the invention is shown in FIG. 1A. A multiplicity of emission wavelengths are produced by LED array 30, scattered from a material 32, and detected by photodetector array 34. An optical barrier 36 serves to reduce the amount of light from array 30 that directly travels to array 34 without interacting with the material 32. An LED controller 38 serves to activate the LED array 30 in accordance with patterns specified by a signal processor 40. Signal processor 40 also analyzes signal data from array 34 which is acquired by a data acquisition circuit 42. A database 44 is used to store the analyzed data from known materials for comparison with data from unknown materials.

The operation of this embodiment includes the following principles. If the same applied optical frequencies and geometry are reapplied to the same or a similar material, the same or a similar matrix of detected signals should prevail. Consequently, through comparison algorithms, an unknown material could be identified as the same or similar to that measured previously. Therefore emitter array 30 and detector array 34 can be "trained" to recognize a certain class of materials by recording the detected matrix of throughput signals from several samples from the class, and comparing corresponding signals from the unknown material. It is important to note that since the signals have a dependence on the emitter-sample-detector geometry, the geometry can be used as a further parameter for classification.

In the IDEA probes according to the present invention, different wavelength combinations can be simultaneously or sequentially applied via computer control. The individual LEDs in array 30 can be independently controlled so that none, one, several or all LEDs are activated at any given moment. At least two regions of the material play an identifying role in the optical examination of materials: the surfaces and the bulk. Impinging radiation is reflected/refracted at the entering surface and refracted or totally internally reflected by the exiting surface. Absorption, transmission and bulk scattering occur primarily within the bulk. These properties, and various others, constitute the matrix of information useful to identify the test object or material.

Thus the absorption/emission properties that affect the probe's measurement inevitably contain information about the optically absorptive states in the material and the electronic interactions between such states in the material. These measurements are invariably unique to certain specific properties of the material. In this manner, even without determining values for the differing densities of states or the rate constants for kinetic processes between those states, the ensemble interactive effects in the probe's detected signals over all applied wavelength combinations contains an absorption/emission signature for those processes. The material can thus be discriminated and identified from other materials by such optical interaction signatures which contain implicit density of states information. It is furthermore possible to use one or more of many other possible material properties as additional variables used in conjunction with each optical measurement set for analysis, discrimination, or identification processes. These additional variables might include, for example, magnetic susceptibility or conductivity. In the latter case the prevailing electric field between two electrodes and the electrons flowing in or out of each electrode pair (i.e. the energy per quantum and the quanta per second) can be determined and used as additional variables. In semiconductor materials such measurements can help elucidate the density of available states as well as excited carrier lifetimes associated with those states. In addition, thermal properties of the material can be utilized as an additional piece of information by adding a temperature sensor in the probe tip. This thermal information could be used as an identifier or else to control or monitor the LED temperature.

In one embodiment the array 30 comprises LEDs having N=15 distinct wavelengths, with representative LEDs labeled A, B, C, D, E, ..., X, N, O. When these LEDs are taken in any combination there are about $2^N-1=2^{15}-1=32,767$ possible illumination combinations. One of the novel advantages of this spectrometric analysis of materials using a combination of junction emission sources (like LEDs) is that most combinatorial composite spectral envelopes are synthesizable via computer, i.e., from one single narrow peak to any combination of 15 peaks. This allows the possibility of detecting non-linearities in material properties at lower optical intensities than with single peak spectral beams. When a conventional single wavelength is applied to a material, its intensity must be sufficient to begin to "saturate" some occupied density of states at the energy. But since only a small non-linearity results from a large applied intensity, the non-linearity is thus difficult to resolve. However, when the detected interaction effects of two overlapping wavelengths (A and B) are measured, their algebraically, detected sum (A separate+B separate), and their combined superimposed sum (A+B, simultaneous) can be readily compared to say, 16-bit to 24-bit accuracy (i.e. to 1 part in 65,536 or 1 part in 16,777,216). That is, if both applied wavelength distributions remain identical before, during and after their interval of overlap, any differences in the detected separate-algebraic sums and their detected simultaneously-applied sums can be resolved to parts per million. But the control computer can, in this example, actuate 32,767 such combinations of 15 applicable LED wavelengths and look for differences in their separate-algebraically calculated and the simultaneously-applied measured sums. Any differences constitute signature bearing discriminations useful to identify the material. Such differences relate to available density of states in the material; and the occupancy of such states is influenced by the rate-occupancies transfer between available states under applied excitation. Such rates are also influenced by lifetimes of excited carriers in those states and so transition rate lifetimes influence the dynamically detected responses during 32,767 applicable combinations. If in fact, the detected signals in the IDEA probe vary under the same illumination between the consecutive A/D conversions, (e.g. every 10 micro sec), then the influence of long excited carrier lifetimes in the material can also be utilized as discriminators in identification algorithm.

Reiterating, let each detector output feed a 16 bit A/D converter having 1 part in 65,000 resolution. If all wavelength intensities (photons/sec) were applied without interacting with each other for each of these 32,752 combinations, [say A+B+D] the sum of separate detector responses measured for A, B and D each illuminated separately when algebraically combined to within one part in 65,000 should equal the detector response under the combined illumination of A+B+D. To the extent each of those 32,750 combined illumination measurements do not equal the respective additive sum of their separately added measurements there exists some interdependence between the applied wavelengths. If such interdependence exists the IDEA probe algorithm can detect them through simple arithmetic; the detected output when A, B, and D are superimposed minus the computed sum for separately detected outputs of excitations A, B and D. Of course not all 32,750 combination illuminations need to be applied, measured and checked out by algorithm to glean some indication of prevailing non-linear interdependencies. A judiciously selected 1000 or so combination illuminations can tell the computer whether to irradiate the sample material with more combinations to thoroughly evaluate the circumstances.

This requires that detector linearities must be excellent over a large dynamic range and PIN detector devices are linear over 7 to 9 decades. Emission sources are typically less linear than PIN detectors but the LEDs can be driven under identical conditions whether their irradiation is individually or simultaneously superimposed. Having LED die thermally coupled with appropriate substrate design to a large heat sink, the superposition of 15 different wavelengths can readily provide photon emissions to 1 part in 65,535 repeatability when the separation in time is milliseconds. The computer can also compensate for small detector and emitter non-linearities and temperature effects if they are stable. Because measurements at the same respective LED currents can be taken within milliseconds, thermal effects between distinct illumination combinations can be negligibly small. In this manner, without actually having a model for the density of optical states within the material and the rates of electron transfer between those states, a signature about those processes become available through probe data. If one assumes elastic scattering is very linear then such scattering does not contribute to the measured, non-linear signatures, and only absorption processes would be non-linear. Thus, in addition to enabling identification of the material, the data can be used for analysis purposes to provide separate information about the scattering, absorption, the density of states and the rates at which particles transfer to and from those states. When such analysis is a primary goal, the algorithm might well illuminate the sample with all 65,535 combinations and so attempt to ascertain the density of states information about materials as yet another application of the probes discussed herein.

A prime reason why virtually all optical-to-excited electron-phonon systems are slightly non-linear relates to the prevailing mass actions probability of particle transitions between any pair of states where transitions occur. If for example N excited electrons at some energy level recombine into P available states then the rates at which such recombinative transitions occur are in proportion to N times P. Since N and P are both dynamical variables that change with optical excitation, rate equations characterizing the reaction kinetics between states will be fundamentally non-linear to the extent that any P (or N) is not constant over all encountered levels of excitation, or over all wavelength combinations. It is generally assumed (for simplicity in modeling a complex set of slightly non-linear equations) that each P (or N) can be treated as a constant thereby allowing the system to be simulated as linear, thereby greatly simplifying analysis. But linear equations are a special case of non-linear equations which are always more general, and the prevailing mechanism is fundamentally non-linear.

The IDEA probe can simultaneously apply any or all combinations of excitation wavelengths and search for non-superposition whenever the difference between the combined-applied detected signal and the separately applied algebraically summed signals does not equal zero. Such a non-zero difference can be caused by any combination of N and P mass-action variations over all ranges of N and P encountered, or by any non-linear effect which prevails from any source. The non-zero difference for the 32,767 comparisons provides a signature of that material. This measurement of optical non-linearity via a deviation from zero is a new and powerful form of spectroscopy that forms an essential feature of this invention. We call this new technique multiply added spectra (MAS) spectroscopy. If each measurement of the 32,767 took 10 microseconds than a material can be completely scanned for non-linearities in 327,767 microseconds, or about ⅓ seconds.

Besides applicability as a material identifier, for any given material the non-zero difference signatures (along with respective optical excitation energies) can be used to help model the prevailing recombination processes. It is a significant feature of the present invention that the identification capabilities do not require any model for the ongoing processes within the material in order to match the material to a pretrained set. However complex the recombination processes that occur upon excitation, knowledge of them is unnecessary to obtain their signature. Thus such non-linear signature analysis can be highly useful for non-invasive identifications, analysis and quantizations in blood, tissue, minerals and the like. Applications which include the in vivo non-invasive determination of glucose levels, lipid profiles, cholesterols and percentage of tissue constituents using these techniques are incorporated within this description. Large molecules and cells are likely candidates for such measurable non-linearities.

Low light level non-reciprocity effects in film demonstrate a prevailing example of non-linear optical effects in material. It is an example made familiar by having exposed and extensively tested film under a wide variety of optical wavelengths and intensities under conditions of precise measurement. Many other materials possess non-linear effects but they have not been similarly scrutinized for optical non-linearities. This can be achieved simply with probes described herein permitting independent simultaneously-applied or separately-applied wavelength combinations under conditions of highly accurate measurement, that sum to zero in the absence of non-linearity. Namely, each non-zero (off-null) difference provides a direct numerical indicator of the prevailing degree of non-linearity.

Consider again the emitting/reflecting IDEA probe in FIG. 1A. where N discrete LED emitters in the array 30 are optically separated from the detector array 34 by an intervening optical barrier 36. Within the probe interior photons emitted by each of the sequentially illuminated LEDs are prevented from reaching any of the detectors by the optical barrier 36. In the absence of any sample material 32 within the field of view, unwanted crosstalk between the emitting array 30 and detector array 34 is fixed and made undetectable or negligibly small because of the optical shield 36 which surround each compartment except at its optical face. Radiation from the emitters emanate into the exterior field of view, a portion of which includes the object 32 being tested. In the material sample 32 the photons are scattered and retroreflected and some fraction reach the detectors. Signals from the detectors are respectively amplified, multiplexed and fed to one or more analog to digital (A/D) converters in a data acquisition circuit 42. The digital signals then go to a signal processor 40 where they are processed and used in a decision algorithm which compares them with the variables derived from measurements of previous trained reference materials. The signal processor is thus able to determine into which pretrained category the unknown material properties best fit.

Figure 1B:
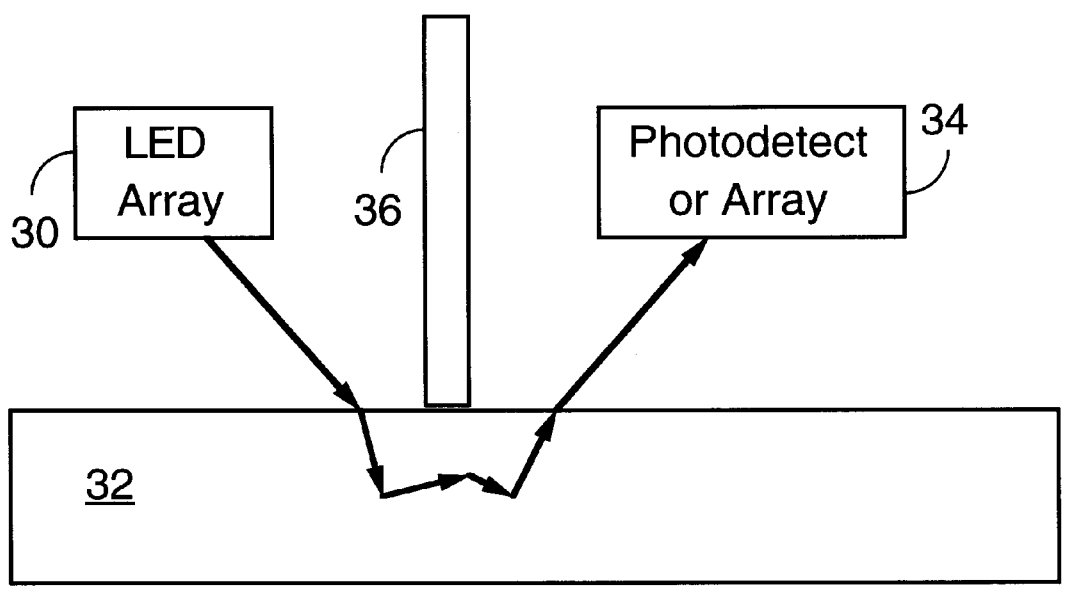
FIG. 1B is a block diagram of a preferred embodiment of the invention wherein the optical barrier is touching the object surface.

FIG. 1B shows the optically functional elements of the probe in the case where the distance between the optical barrier 36 and the material 32 is very small or zero. Consequently, the surface reflected signal present in FIG. 1A is reduced or eliminated in this case, and only bulk scattered light is detected by the array 34. Therefore, by changing the distance between the optical detector and the material surface, different radiative interactions can be isolated for measurement and used to enhance material identification, as will become apparent in the description of specific embodiments below.

The present description calls each discrete detector element a pixel and its respective amplification-digitization-storage channel a pixel channel, although these elements are not necessarily arranged to form a conventional XY type pixel array, but could have any geometrical arrangement. In addition, this description calls each discrete LED radiation element a RADEL and its respective driver circuit a RADEL channel, again recognizing that these elements are not necessarily arranged in a conventional XY array, but could have any geometrical arrangement. The throughput from a specific RADEL element and a specific detector pixel element derives from that RADEL/PIXEL channel. The total ensemble of LEDs is called a RADEL array analogous to a CCD or CID pixel array. It can be observed that a symmetry exists with respect to image formation between a pixel array of detectors and a radel array of emitters, which when appropriately driven and sensed by each detector can also form images and radiometric cameras in analogy to flying spot scanners.

Figure 2A:
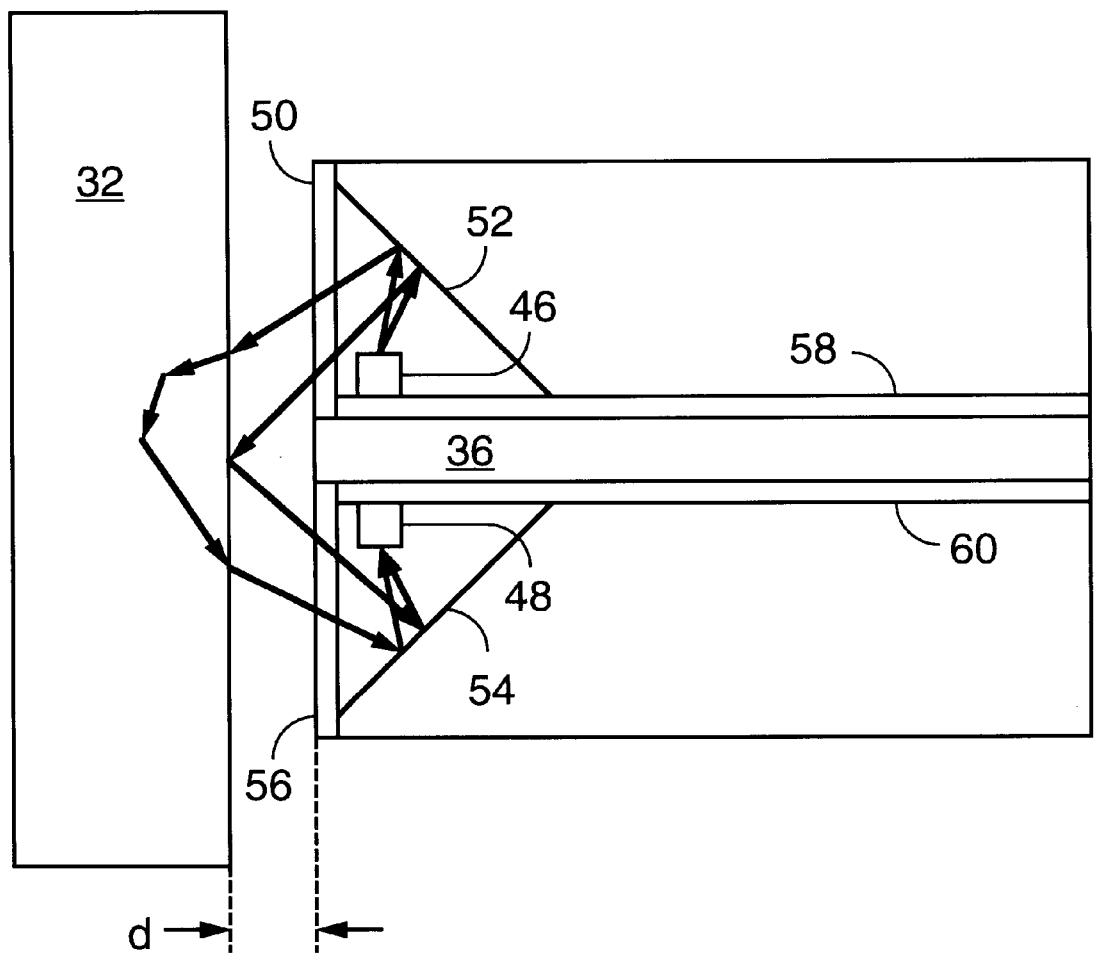
FIG. 2A is a cross-sectional view of a particular embodiment of an IDEA probe.

FIG. 2A is a cross-sectional view of a particular embodiment of an IDEA probe. The probe can be moved off the surface of the material 32 any distance d. Emission from the sequentially activated LEDs 46 emanate from the probe through clear epoxy 50 or polymer protecting the LEDs. A portion of each LEDs emission is reflected off a reflective surface 52 that is part of the probe's metallic housing. This output emission reaches the surface of the material under test having a quasi-Lambertian distribution. Some radiation reflects or scatters from the material surface itself, or very close thereto, and some penetrates slightly, scatters, emanates and enters the clear epoxy 56 protecting the detectors. A reflective surface 54 similar to surface 52 serves to direct the radiation to detectors 48.

The LED drive electronics 38 (FIG. 1) is fixed upon an LED printed circuit board (PCB) 58 which is enclosed within the metallic housing of the probe. Similarly, the detector electronics 42 and other signal processing elements 40 are fixed upon a detector PCB 60 which is also encased by the metal housing of the probe. When objects in the field of view are far from the probe surface, negligible radiation energy reflects back to the detectors, since distance d is very large. As the probe is brought closer to the material surface, the amount of detected radiation increases, primarily due to reflection from the material surface. When the probe is in contact with the surface, the detected radiation is primarily due to bulk scattering.

Figure 2B:
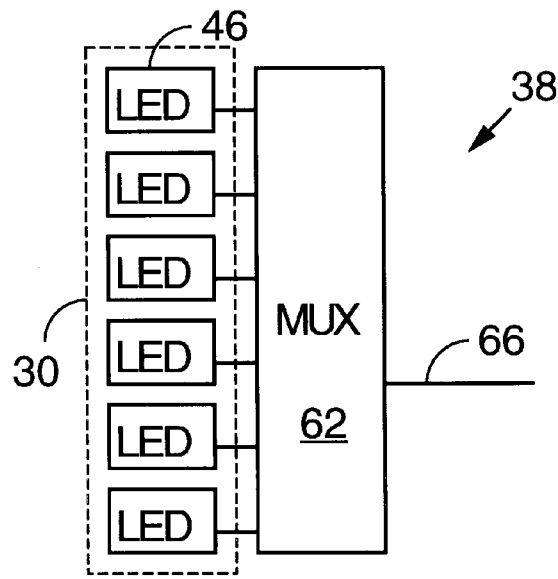
FIG. 2B details the drive electronics of an LED PCB.
Figure 2C:
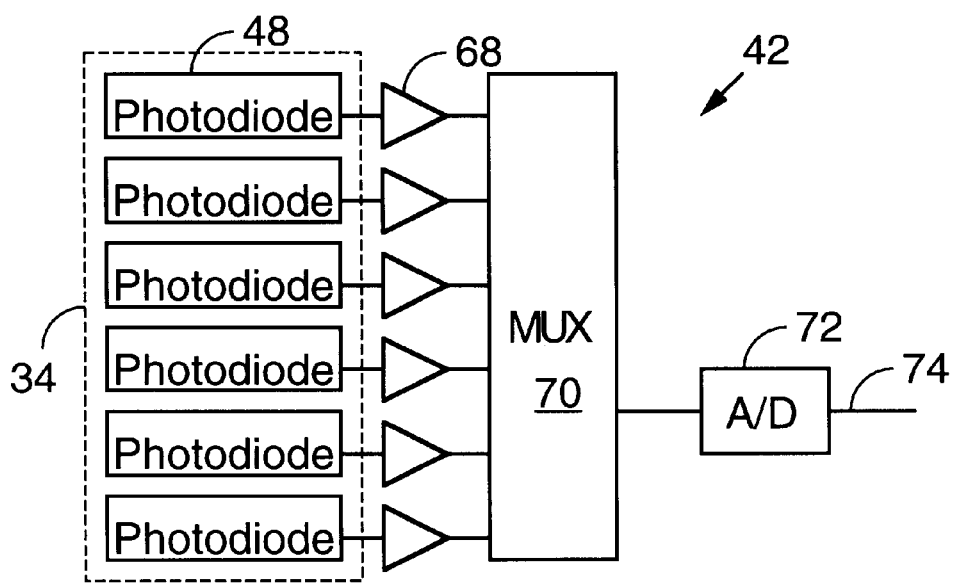
FIG. 2C details the detector electronics 42 of a detector PCB.

FIG. 2B details the drive electronics on LED PCB 58. The LEDs 46 are arranged in a fixed geometrical array configuration 30 and connected to a multiplexer (MUX) 62 for driving the array. Note that MUX 62 may be discrete analog switches. Multiplexer 62 is provided with an LED control signal 66 from the signal processor 40 (FIG. 1) for activating specific combinations of LEDs. Thus many different wavelength combinations may be sequentially generated by the array in response to the signal processor. FIG. 2C details the detector electronics 42 on detector PCB 60. The photodiode detectors 48 are arranged in a fixed geometrical array configuration 34 and each is connected to a corresponding amplifier 68 for amplifying the signal representative of the radiation incident on the detector. The amplifiers 68 are connected to a multiplexer 70, which in turn is connected to an A/D converter 72. The digital signals from A/D converter 72 are then fed to the signal processor 40 through a signal line 74. The signal processor may be placed on either the LED PCB 58 or the detector PCB 60. When a specific LED combination is activated and the resulting light from the object is detected by the detector array 34, amplified outputs from each of the detectors 48 are sequentially multiplexed by multiplexer 70 into one single serial information channel before A/D conversion of that channel by A/D converter 72. Alternatively, multiple A/D converters, one associated with each detector, may be used.

Figure 2D:
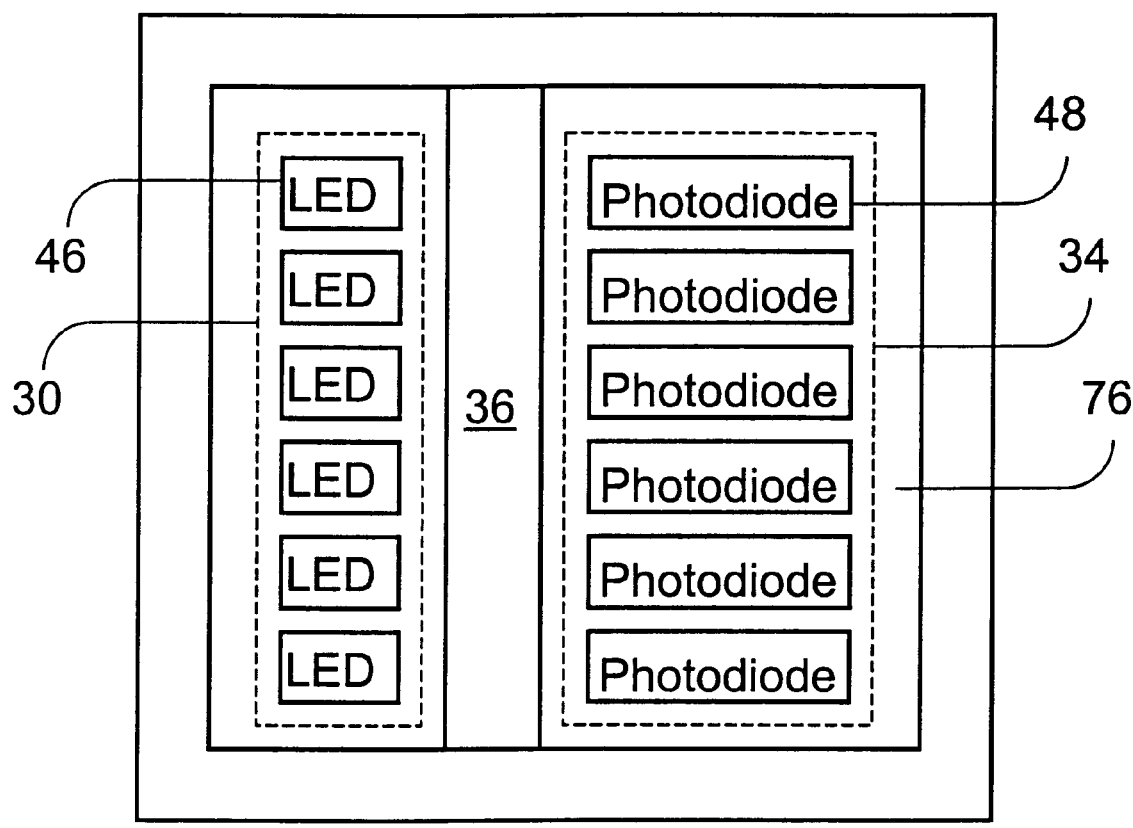
FIG. 2D shows an embodiment in which the LEDs and detectors are mounted on the same side of a single planar substrate.
Figure 2E:
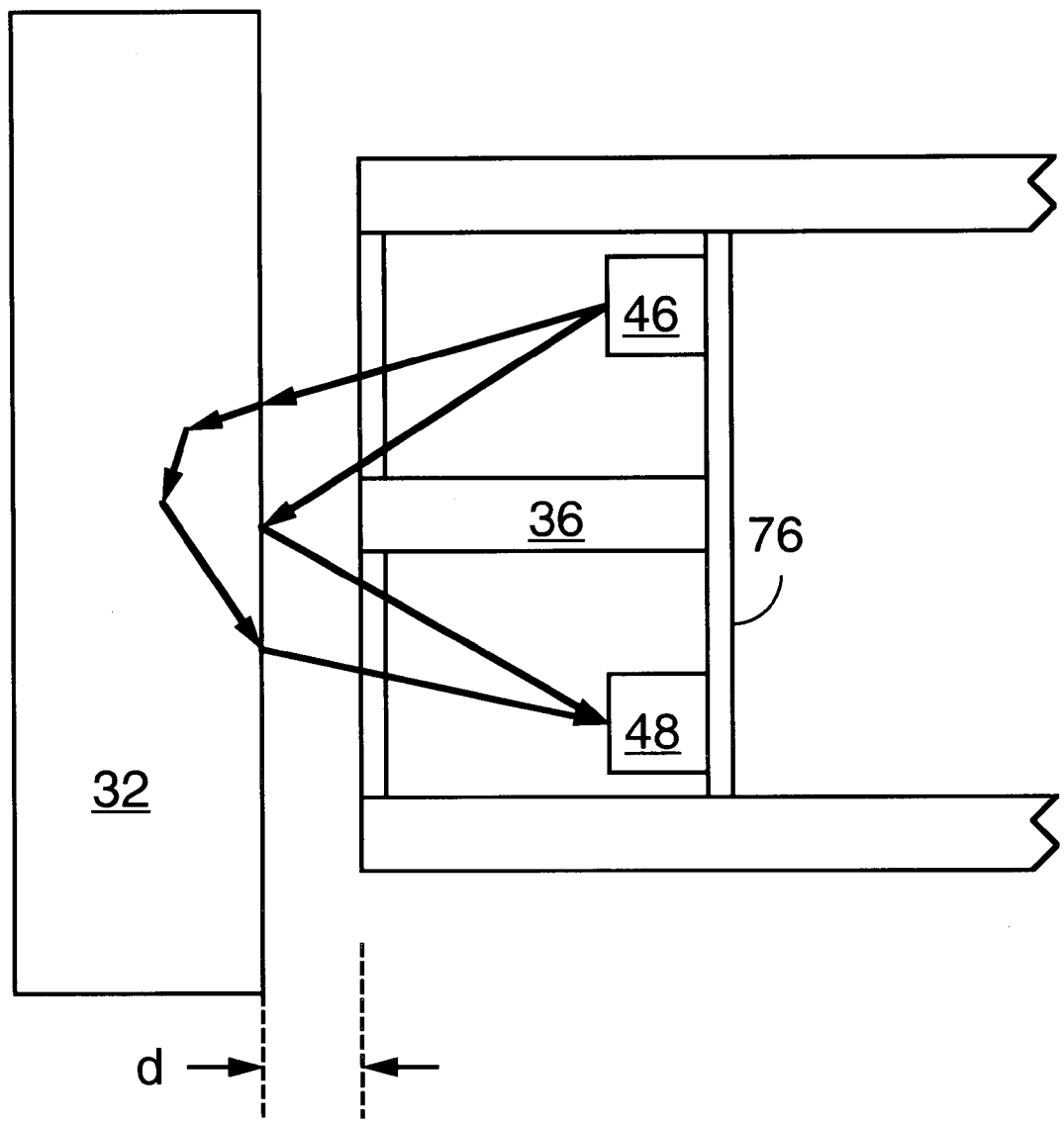
FIG. 2E is a front view of the probe of FIG. 2D.

FIG. 2D shows an embodiment similar to that shown in FIG. 2A. In this case the LEDs 46 and detectors 48 are mounted on the same side of a single planar substrate 76. A front view of the probe of FIG. 2D is shown in FIG. 2E. Substrate 76 contains all the electronics shown in FIG. 2B and FIG. 2C, as well as the signal processor 40. Planar substrate 76 may be a printed circuit board having discrete elements, or a single integrated circuit. In this embodiment, there is no need for reflective surfaces 52 and 54 (FIG. 2A). This embodiment is otherwise the same as that shown in FIG. 2A.

Although the detectors 48 may receive background radiation from ambient light or from an intentional constant illumination source, such detected light can be circumvented as signal variables because they are not temporally coherent with the flashing sequence of the LEDs. A synchronous detection scheme (either digital or analog or software) is used to only register as an optical signal variable (OSV) that detected radiation incremental increase above the background (with all LEDs off) which occurs when each respective LED goes on. This subtraction of the background signal level obtained with all LEDs off enables exclusion of the ambient radiation as a component of the optical signal variables (OSV). If, without overlap of on-time, all N LEDs are sequentially and separately illuminated (including one condition where all LEDs are off) the number of different signals per detector would be one plus the number of LED emitters (N+1). For M detectors this should be multiplied by that number of detectors M to get the total number of different signal variables measured per repeat cycle, i.e. (N+1)M. The number of OSV would be NM when the background illumination is subtracted out. Namely, each detector, of which there are M, has separate output when any specific LED is on, and there are N such LED on-intervals, so the total number of variables equals (N+1)M, and NM of these are OSVs with M being background variables. In certain circumstances the M background variables can be directly used in the algorithm also. Each of the NM signal variables is derived by subtracting from each respective detector output (via software or hardware) the closest-in-time background illumination variable measured by that detector. In normal ambient illumination environments whenever objects in the field of view are far from the probe surface, each detector will have an output that is the same whether any LED is on or off. In that circumstance all OSVs will be zero upon subtraction of the respective LED off conditions.

As the probe is brought closer to the test object, which eventually encompasses the probe's entire field of view, the NM optical signal variable values increase from virtually zero to a respective value related to spectral and spatial properties of the test object. Though the ambient light received by each detector may increase or decrease in this process, its influence is excluded by subtraction as a component of the synchronously detected OSV channels for N LEDs. This eliminates background light from the measurements, provided the sequential sampling rate of LED off conditions is high compared to changes from the motional rate of changing probe positions. That is, negligible motion or change in ambient light should occur in the time between each measurement OSV and its off condition. This is readily achieved for even one off sampling per (N+1) sequential LED on-and-off intervals, (one being an all-off interval). If necessary an off interval can intercede between each on LED when the background illumination changes rapidly.. The influence of background illumination on the data acquired is thus accounted for in analysis.

To clarify further, the M variables derived while all LEDs are off provides a measurement of background radiation at the probe at each such moment and (because the system entails statistically linear superposition of optical and electrical signals) they can be respectively subtracted (by software or digital or analog circuitry) as the then prevailing illumination background. Thus while NM+M variables are measured per full frame of (N+1) sequential LED on and off intervals, the M background ambient radiation measurements within each frame, when respectively subtracted from the others, leaves NM optical signal variables. These constitute the OSV signal variables acquired in room light though they are independent of that ambient radiation. They are used to characterize the test material as described hereafter. The system can thus operate as described in spurious ambient illuminations virtually without detriment. It should be noted that all the LEDs are not necessarily of different wavelengths. In general there may be a factor of Q redundancy so that the total number of LEDs is QN. For example, if there are two LEDs of each wavelength (Q=2), then the total number is 2N. The differing spatial positions of the two similar LEDs provide them with unique information generating capacities.

Figure 3:
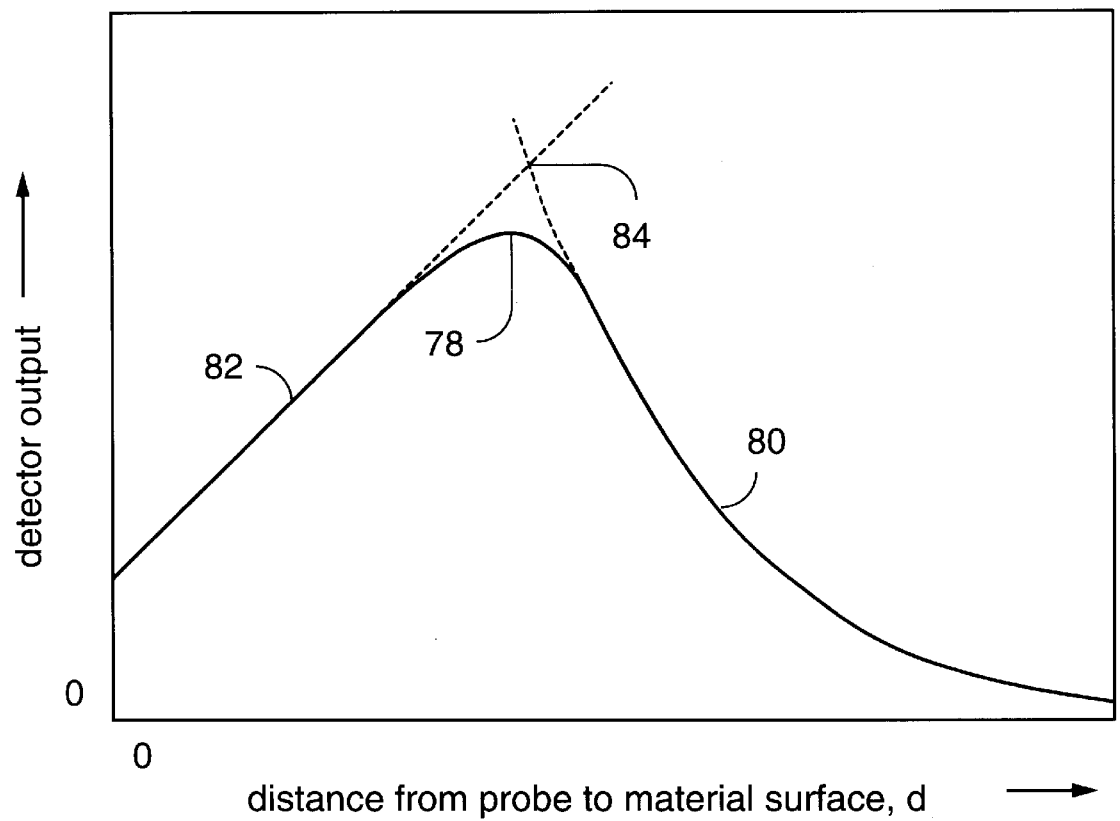
FIG. 3 is a graph showing the magnitude of OSV variation with probe-to-material distance, d.

For a quasi-homogeneous field of view, as the probe-to-test-object distance d is reduced from a large value, OSV values typically vary as $1/d^2$, as shown in FIG. 3. This constitutes the region where the detectors sense primarily surface reflectance properties of the material; and of a background upon which the material rests if the material is relatively small. Eventually however the object comprises the probe's field of view so that only its material is being viewed. As the probe gets even closer (relative to the emitter-detector spacing and intervening optical barrier thickness), that barrier begins to obscure an ever greater portion of radiation that would be reflected from the test object's surface. In this region, the OSV values vary in rough proportion to the distance d.

When the IDEA probe comes into contact with the surface (i.e. d=0), no surface-reflected photons can reach the detectors. This is the condition under which only bulk properties of the material are evaluated. Emitted photon density is greatest at the probe surface and in order to reach the detector such photons must scatter through the material a distance comparable to the optical barrier thickness and into the detector compartment. For each RADEL channel this entails transmission/scattering through the bulk material back to all pixels, as affected by their spatial positions relative to the specific emitting LED. The net result is that in one motion of the probe to and from the material both the surface reflectance properties and bulk properties of the material can be ascertained. The IDEA probe can also be immersed in liquid or gas or powder, thereby analogously indicating and identifying spectral properties of such materials. An important feature of these probes is the diversity of materials that can be measured with the same probe.

An indication of the value of utilizing bulk optical properties as a material identifier in addition to surface optical properties is given by the following considerations.

1) In the case of a "flat" white reflective surface having surface reflectivity close to unity (maximum) over the visible and near infrared region, there is very little information in a reflective response. One must look at changes or derivatives with respect to photon energy in the spectral response to obtain the signature information. Very few materials, however, maintain high bulk reflectance over an extended frequency range. With the exception of clear, nonscattering materials, bulk reflectance will vary with wavelength due to scattering from particles of given size contributing different scattering for different optical wavelengths. Bulk reflectances generally vary extensively with wavelength and thus yield good signatures of the material. Rayleigh scattering typically varies as the inverse fourth power of wavelength and applies to particles whose size is less than a wavelength. Mie scattering applies to spherical particles whose size is comparable to or greater than the wavelength and approximately varies as the inverse square of wavelength. Because materials which have a flat bulk reflectance over visible and NIR wavelengths are much more rare than materials which have a flat surface reflectance, the bulk scattering information of an unknown intrinsic material is usually more useful for identifying the material than its surface properties. Excepting metal solids, bulk optical properties versus wavelength are usually measurable by IDEA probes if the optical barrier is sufficiently small.

2) Most light seen in an image is the result of optical scatter off surfaces of materials within the scene. The 180 million photoreceptors of each eye and brain channel have been trained by experience and genetics to identify scene objects from these signals. Factors like gloss,. texture, diffusivity, hue, shadowing, and saturation, are influential discrimination parameters used in the eye and brain signal paths. Surface finishes are easily scratched, weathered, deformed, bleached, erased, dirtied, etc. These effects can produce significant variations in the power spectral density function from surfaces, effects that are not present in subsurface measurements. For vision, variability of these parameters requires a great number of spatial detectors and an extremely elaborate information processing system, i.e. the eye/brain. By ascertaining subsurface bulk scatter with the IDEA probe in contact with the material, ambiguities arising from these inadvertently changeable parameters can be minimized in the identification process, yet these parameters can be separately detected in the probe's approach. In measuring biological samples, for example the primary relevant element which produces scattering (because of numerous membranes) and requires identification, is the cell. The IDEA probe is configured so that the analysis algorithm has the option to subtract, or partially exclude, surface variable phenomena and examine primarily the scattering from those elements that identify the unknown entity, the cell. The same design criteria are equally useful for many materials having any small degree of bulk scattering, i.e., most materials other than unpainted metals and the like. In a typical IDEA probe the emitter/detector signal throughput from a highly retroreflective scatterer at each wavelength typically exceeds the noise level by 60 dB (1000 to 1). This leaves enough throughput for even very poor bulk retroreflectors like painted metals where even the one or two thousandths of an inch of scattering thickness layer through the paint can optically help identify the object. The same is true for seemingly opaque materials like rock, organics, carbon, thin film coatings in general; or the converse case of clear items like water solutions, alcohols, clear esters, clear plastics, glass, etc. It is noteworthy that for each given on-LED the scattering/transmission pathlength to each detector is different, and with the probe in contact these differences provide a signature of turbidity.

3) The effectively high numerical aperture of the photon distribution (it can be virtually Lambertian) emitted from the probe surface reduces sensitivity to throughput variations through the unknown material because scattered radiation becomes approximately isotropic within turbid materials and thus the source-radiation's angular distribution undergoes minimal transition upon entering the material. This is in direct contrast to utilizing a beam of radiation to impinge upon the material. This generally means that right from the surface inward the photon density follows the diffusion equation and is amenable to precise computation, a condition not valid for incident beams.

4) Because many surface properties are directly visible, surface reflectances do not add much additional identification information above what the human eye can see. IDEA probe information augments visual information well when both are utilized to classify objects.

A typical pattern exists as to the general magnitude of OSV variation with probe-to-material distance, d. FIG. 3 depicts the variation in relative signal output with respect to the distance d. A peak 78 in OSV output is located between an inverse square region 80 and a linear region 82. The inverse square region 80 corresponds to larger probe-material distances where there is an approximately $1/d^2$ variation in reflected photons back to the detector surface. The linear region 82 corresponds to small probe-material distances where there is a quasi-linear variation in output with respect to distance d due to obstruction from the probe's optical barrier. The linear and inverse square curves intersect at an extrapolated intersection point 84 located above the actual curve. By making successive measurements throughout a continuous monotonic variation in the probe-material distance, the probe can determine the peak value 78 and the intersection point 84, and use these points, which represent a combination of surface and bulk features, to assist in recognizing the material. In this manner both the sample's surface properties and bulk properties are ascertainable independently and in conjunction with each other, and all these can be compared to pre-trained reference properties. The embodiment allows determination of the independent surface and bulk spectral and spatial material properties through a simple "touch of a pen" probe. It is also noteworthy that if within the probe the thickness of the optical signal barrier varies along its length such that larger wavelengths require longer pathlengths within the material to reach certain detectors, the influence of imperfect optical contact can be made less critical.

The composite characterization of the object's optical variables as the probe approaches, contacts, and leaves the object surface provides sufficient information to identify or reference the material property class. In a simplified analogy to the way a CAT scan reconstructs a spatial image through deconvolution of the variables it receives at different positions, a composite algorithm can ascertain the best match between the object and pretested classes of objects. Alternatively, if a series of 100 unknown object properties (say numbered 1 to 100) is sequentially tested by the probe, the algorithm can sort these properties into a predefined numerical order or separate groups depending upon their optical similarities and differences in accord with predetermined criteria. Using an algorithm, quantitative optical characterization numbers can be assigned to any combination of OSVs and to each property. Thus sorting, zoning, monitoring, classifying and identifying are all possible functions of the probe with or without a pre-acquired library for comparison purposes.

Discriminations of this type are typically achieved using algorithms based upon discriminant analysis, principal component analysis, feature extraction, Bayes theorem, genetic algorithms, decision trees, least mean square differences, artificial neural networks, wavelet theory, pattern recognition algorithms, syntactic analysis, artificial intelligence, polynomial classifiers, Walsh transforms, fuzzy logic and fuzzy logic trees. They may operate either dynamically with probe motion or statically while in contact, either on-line in real time, or off-line long after data acquisition. Such algorithms as well as customized variations and improvements of these and other proprietary algorithms can be devised for generic or specific identifier probes employed in this invention. With varying precision, algorithms based on these methods can sort degrees of similarity between an ensemble of optical scattering variables with another ensemble of optical scattering variables. Such procedures can determine into which category an unknown ensemble best matches those of a plurality of referenced ensembles. They can hierarchically order the likelihood of association between arbitrary sets of optical variables. This means they can probabilistically determine which of a group of past evaluated ensembles an unknown ensemble comes closest to and furthest from; or which ensemble that comes along in the future is closest or furthest from one at hand.

Embodiments can be readily configured for many applications such as, for example, minimally invasive medical screening, food inspection, process control, fauna or flora research, industrial material inspection, production line quality control, cosmetic and camouflage comparisons, environmental monitoring, general liquid, powder, and solid identification, fluid and gas flow monitoring, and ore separation. The identification achievable is highly utilitarian and easily made portable. Some example embodiments will be described in greater detail below.

A fundamental feature of this invention is that a single probe can be used in a large variety of commercial applications, despite the fact that it has a fixed spatial arrangement of LEDs driven by a predetermined circuit and employing a predetermined generalized algorithm. This has many advantages in reducing the cost of design and manufacturing. Because it can be expensive to manufacture a device having N different wavelength LED die in a single assembly with tight specifications on each LED type as N becomes large, requiring the least number of manufactured assemblies greatly minimizes die positioning equipment costs and fabrication difficulties. Typically, die positioning machines operate from only one or a few wafers to form an assembled hybrid semiconductor product. LEDs of different wavelengths generally derive from different III–V or II–VI alloys. A manufacturing process that accurately selects and positions die from 15 or 20 wafers onto a single assembly of arbitrary shape can be very complex and expensive. Therefore it is desirable to minimize the different kinds of such assemblies by devising a large number of applications for each assembly that is to be fabricated. An important advantage of this invention is that a relatively few arrays of N different wavelength LEDs and arranged in with predetermined spatial dimensions and configurations (e.g. linear or circular) can be used for a large variety of commercial products thereby making all of these products cost effective. Without such multiple applications of the same assembly, each of the products might not be economically viable.

The probe shown in FIGS. 2A–2E depict a probe having RADELs and pixels in linear spatial configuration. These elements, however, could also be arranged in an unlimited number of other spatial configurations. For example, the emitter and/or detector elements can be arranged to form any arbitrary 1 dimensional curve, such as a conic section (circle, ellipse, hyperbola, parabola) or portion thereof, a polygon (e.g., triangle, square, pentagon, hexagon), or portions thereof. The elements can also be placed with varying degrees of density to cover a 2 dimensional surface. Such surfaces may be flat or have curvature.

Figure 4A:
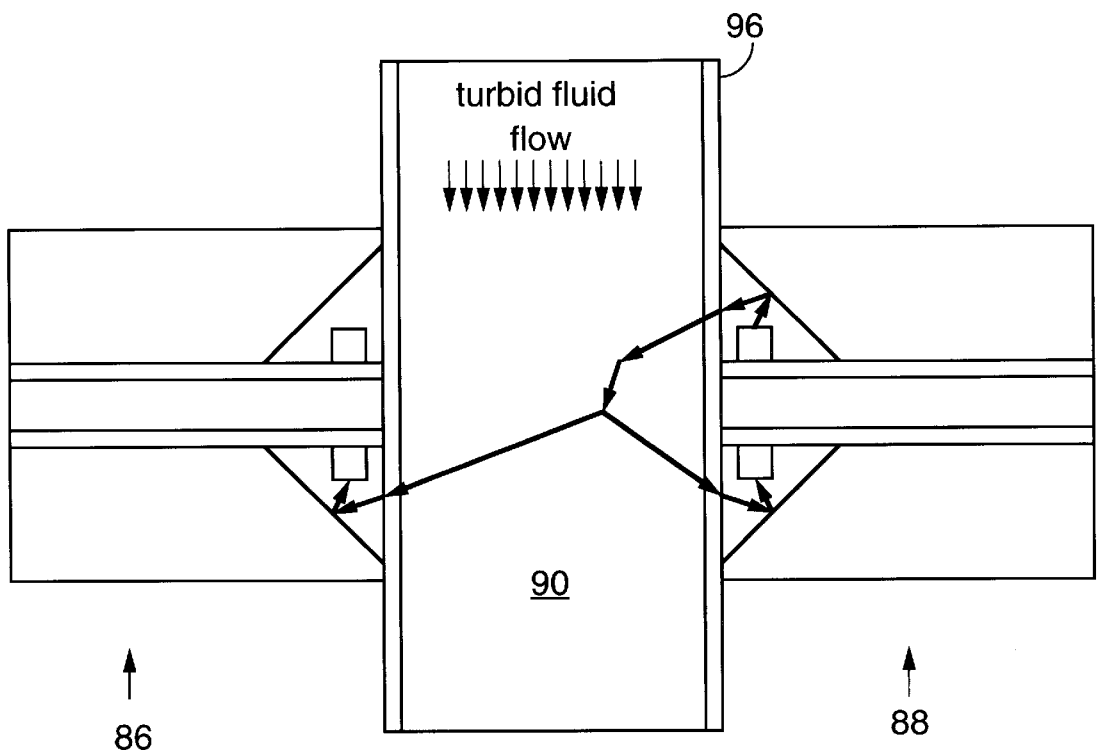
FIG. 4A is a cross-sectional view of two IDEA probes facing opposite sides of a central examination region.
Figure 4B:
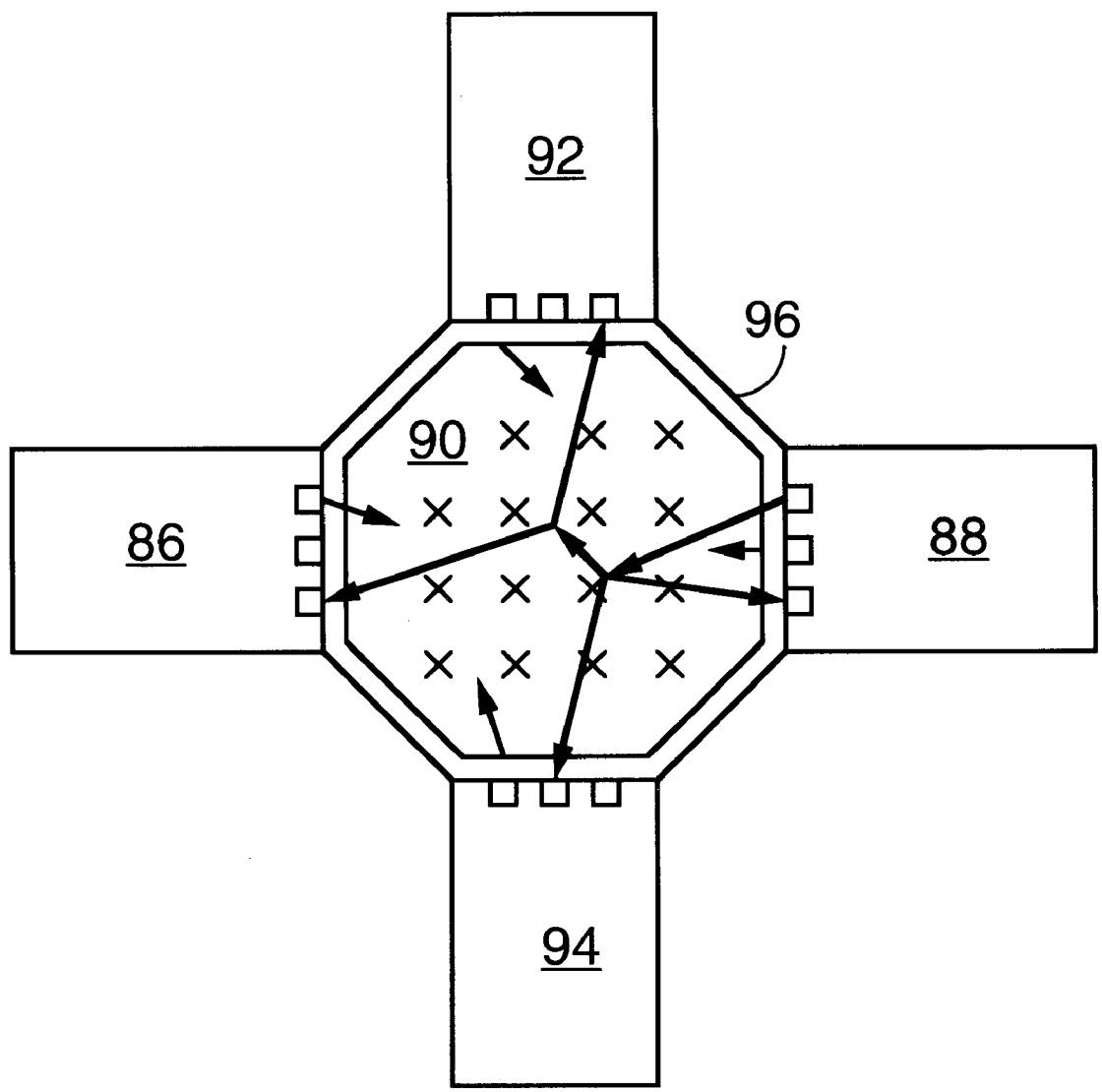
FIG. 4B illustrates an embodiment in which four probes are alligned at right angles to form a square test region.
Figure 5:
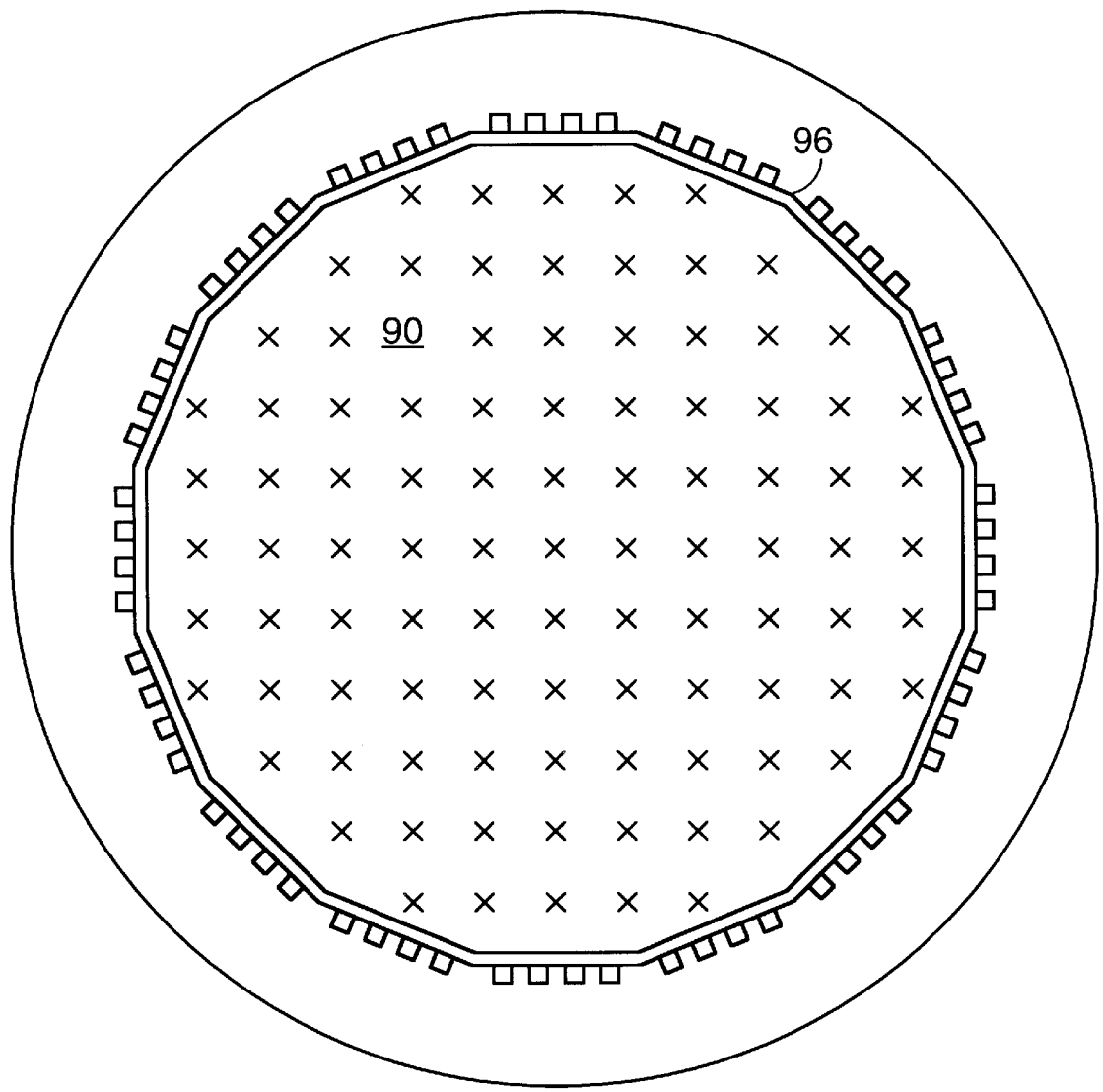
FIG. 5 shows a system similar to that of FIG. 4B but having detectors and emitters positioned on the faces of a regular 16-sided polygon.

FIG. 4A shows a cross-sectional view of two IDEA probes 86 and 88, each similar to those described in relation to FIGS. 2A–2E. The two probes are facing each other with the test material 90 positioned between them. As shown in FIG. 4B, two additional probes 92 and 94 may be aligned at right angles to the first pair to form a square test region which could examine transmissions as well as 90 degrees angular scattering. The different probe LED drivers can be actuated in sequence so all detectors see the output from each LED and these detector outputs are multiplexed to a common signal processor for all four probes. This configuration allows monitoring of the spatial, temporal and spectral scattering, reflection, right angle scattering, and transmission of materials passing through a the enclosed region. Each of the four probes of FIG. 4B can have N wavelength emitters and M detector elements. Between and in contact with their faces can be clear tubing 96 through which turbid fluid or gas flows, or the examination region between their faces can be any area, open or closed, where parts, objects or materials pass through as in an assembly line. The material may be stationary, or moved in any manner within or through the central examination region. In the embodiment shown the probes are considered in fixed contact with the tubing. In one mode of operation, all LEDs of the four probes are activated as would be those of a single probe with 4N LEDs. For each combination of individual LEDs the 4M amplified detector output signals are sequentially multiplexed, so that for each combination, all transmission as well as retro-scattering components commensurate with the geometry are accessible as well as the background illumination. FIG. 5 shows a larger system having detectors and emitters positioned on the faces of a tube having a cross-section in the form of a regular 16-sided polygon. This system operates according to the same principles as just described, but allows additional angular information to be obtained.

Effects of fixed crosstalk from surface reflections of the tubing can be minimized by recording and subtracting in the processor, detector signals that occur with no fluid or gas in the tubing, analogous to cancellation of background radiation. Also, the tubing walls can become the probe face at the region of the probes so there would be no tubing wall reflection. By subtracting the non-flow case from the other cases one can both distinguish between the absence or presence of fluid or gas and the incremental changes when fluid or gas motion occurs. Similarly the differential effects of temperature, pressure or turbulence changes can be identified by subtracting one case from the other for each OSV. Signal variables from the fluid or gas can thus be continually monitored providing a temporal, spatial, and spectral signature of the fluid and of bubbles within.

Alternative embodiments of identifying flow rate as well as constituents (even in clear fluids) entail creating a vortex in the fluid flow via a protruding upstream perturbation into the tubing interior. The resulting turbulence refracts the various wavelengths differently thereby creating noticeable fluctuations in detector outputs. Alternatively, if the internal area of scrutiny is being examined for the passage of objects, items, materials, bubbles, or large particles (in contrast to liquid or gas tubing flow) the temporal, spatial and spectral properties of such objects can be evaluated and identified by algorithms that best discriminate between the different groups of objects. The embodiment starting with two or more identical IDEA probes suggests how applications of the previously described generic LED assembly can be increased by the compound assembly of multiple probes. An analogous situation applies to the use of reflectors rather than multiple probes.

Rather than using distinct PCBs for each face of the ring systems shown in FIG. 5, a single annular PCB can be used. In this system the liquid or gas can flow through the tubing either axially (into the paper) and normal to the ring of LEDs [or between the LEDs and detectors above or below them within "flat" sided tubing (along the plane of the optical barrier)]. The probe can also be directly immersed into liquid, gas or powder. The ring of detectors need not be made of discrete elements as shown but can be replaced by a CCD array (or CID array) of most any circular, linear, polygon or an XY geometry. Here the IDEA probe can be employed in a fixed position relative to the test sample and need not be moved in from "infinity". Indeed, information about the position of each passing particle within the tubing is quasi-determinable by the relative dynamical signals of each pixel element. The decrease in spatial/temporal information variables that result from not bringing the probe to and from the test object can be overcome, at least in part, by utilizing a significantly larger array of spatial variables.

A key feature of this invention is that relatively few LED (and detector) assembly configurations may be used to implement a large number of different applications. As the above example indicates, a few sizes of straight line LED assemblies will suffice for many applications. This particular feature has high economic relevance because different wavelength LEDs derive from a multiplicity of wafers of different diameters, alloy materials, dopants, n or p type, thickness, dimensions, saw cuts, bonding pads, mesa levels, etc. and their die must be assembled onto a single substrate. From the semiconductor foundry there may be 5,000 to 25,000 LEDs per wafer and some wafers may cost many thousands of dollars. LEDs of each specific wavelength may need to be selected from a specific portion of its wafer. LED wafers are manufactured all over the world by different manufacturers involving differing materials, equipment, fabrication costs, cutting methods, and production and instrumentation standards. Peak wavelength outputs may vary by 5% over the wafer area, spectral bandwidths by 20%, and efficiencies ay vary by 4 to 1. Therefore a mapping of each wafer's characteristics over x and y can become detailed and important. The problem of achieving a satisfactory assembly of sizes of wavelength, bandwidth, n or p type, efficiency, bond pad shape and directionality among 15 different wafers made by perhaps 10 manufacturers is very formidable. Often the 15 die must be selected from different respective wafer positions to optimize each specific LED assembly. This is highly untypical of other hybrid assemblies made predominantly of silicon die, not diverse alloy wafers. Each IDEA probe with N=15 would likely derive from 15 different wafers in a manufacturing setup that could potentially produce many thousands of assemblies. The market for one single application might never justify thousands of units. Conventional die pick and place equipment generally do not easily accommodate placing die onto a single printed circuit substrate from more than a few different wafers at most and equipment to do so is very expensive.

Registration problems are formidable for 15 different wafers with regard to accurately attaching N (or 2QN or 3QN) different type, size and tolerance die with thousandth inch precision (here Q is the number of same wavelength LED die). The practicality and economic viability of any single application is greatly increased if only a few different substrate assembly configurations are required for a large variety of applications. Otherwise potential market volume for each such substrate setup might be much smaller than that setup could economically justify. Therefore, manufacturing generic substrate configurations of N die of one repeated design and employing those same substrates in various applications to achieve large production volumes of the same subassembly configuration makes all applications feasible. All applications thus come under one umbrella subject to the cost of manufacturing the key subassembly elements. In effect such generic assemblies become a basic commodity; a utility for multiple uses of which various embodiments will be described herein. Indeed, the generalized embodiment of computer driven different wavelength LED emitter arrays for spectral analysis analogous to CCD pixel arrays for spatial analysis is a feature of this invention.

A large range of different applications can result from IDEA probes fabricated from the same subassemblies. Though in most cases the specific algorithm employed for identification need not to be highly dependent on the precise parameters of each LED and each detector, there are circumstances where spectral and spatial similarity between sub-assembled LED/detector arrays should be well matched or selected for generic algorithm efficacy. Examples of these cases associate with identifying gases with narrow absorption/scattering lines or where any rapid optical change versus wavelength exists in the test material, or where two or more differential measurements are taken at symmetrical positions. Spectrally positioning the skirts of LED fall off can be important in the former case. Differentially comparing similar regions of the left arm and right arm requires matched assemblies and is exemplary of the latter case. There are also cases where matched pairs or quads are designed to be selected to complement each other spectrally via interstitial wavelength peak selection. Fabricating a large number of similar assemblies required for many applications thus makes it possible to then select out those assemblies most closely matched in characteristics to be used in these more critical applications. Those "system" applications requiring tight specifications in the LED parameters [peak wavelengths, bandwidths, and matched pairs, etc.] would not be economically viable were it not for the volume production made possible through having many application embodiments of the RADEL/pixel subassemblies used. The cost of purchasing or fabricating a set of needed wafers might exceed the anticipated end product sales volume of any single application herein. The subassemblies constitute a marketable product in themselves.

The ability to select highly matched assemblies once they are fabricated makes feasible the simultaneous differential comparison of materials, for example in a mill dynamically comparing both sides or both edges of paper or sheet material like plastic, or left/right portions of the body, or products from two process lines or biological experiments. Surface spectral gloss as a function of angle can be measured by utilizing two or more similar IDEA probes mounted on jigs pointing at the same point on a sample allowing independent adjustment of each off-normal angle at the region of reflective bounce while scanning the off-normal angle of the other probe. Such an instrument is typical of IDEA probe systems utilizing the spectral bi-directional (full duplex type) communications of a multiplicity of probes all embodying action at a distance. Other applications include interactively identifying balance or dynamic differences in multiple locations of fluid, particle, or gas flow.

Accordingly, the ensemble of IDEA embodiments articulated in this invention all contribute toward making various other embodiments feasible. The size of the ensemble of the different embodiments using the same or similar assemblies enhances the practical commercialization of each and all these identifiers. In effect such generic RADEL array assemblies, as computer, output spatial/spectral converters of electrons to photons of predetermined wavelength (analogous to pixel arrays being computer input spatial converters of photons to electrons) constitute a basic commodity, a component of multiple uses encompassed by this invention. A feature of this invention is the multiple identification applications for IDEA probes using LED RADELs in conjunction with sensors and electronic computational decision elements. Embodiments of this invention use emitter elements as optical output devices and detector elements as optical input devices. (Single elements can also serve as both emitters and detectors in some instances.) These optical I/O elements convert time sequenced computer electrical output data into spatially and spectrally distributed photon signals, enabling interrogation of the outside world through photon action-at-a-distance. The detectors, on the other hand, convert spectral and spatial information from optical photons having real world information back to electrical input data. Electron-photon conversions derive from near linear computer-compatibility pn junctions permitting density of states surveys of materials. As such the computer (or microprocessor or DSPs as the case may be) can interactively interrogate (through time, wavelength or photon energy and spatial coordinates), within the external physical world without need for electronic or other physical contact. An injection diode (RADEL) array as an area emission line or surface, is an electron-to-photon counterpart transducer of the charge-coupled-diode (pixel) array which represents the photon-to-electron area detection device. Having both such means gives computers capacity to interactively probe X,Y,Z, time and spectrum characteristics of the exterior world. Recognition of RADELs as a computer peripheral "commodity" helps makes apparent the need to produce them in larger volume for many applications. With current-limiting series resistors the parallel port of a contemporary desktop 16-bit computer, within its specifications, can for example provide adequate drive signals to directly actuate 16 different-wavelength LEDs. The timing and sequencing of such LEDs is thus directly controllable through appropriate software. One LED can always be replaced by a non-light-emitting diode to enable monitoring of the background radiation as with the typically referenced 15 LEDs. Greater precision in the control of each LEDs on-current is readily achievable by using intervening amplifiers with constant current output. Additional signal leads available at the computer's parallel and serial ports make it feasible, with external logic, to independently control many times 16 different LEDs. E.g., the PCI bus of a contemporary home computer could support video signals derived from RADEL/pixel arrays having hundreds of LEDs and a million pixels.

Figure 6A:
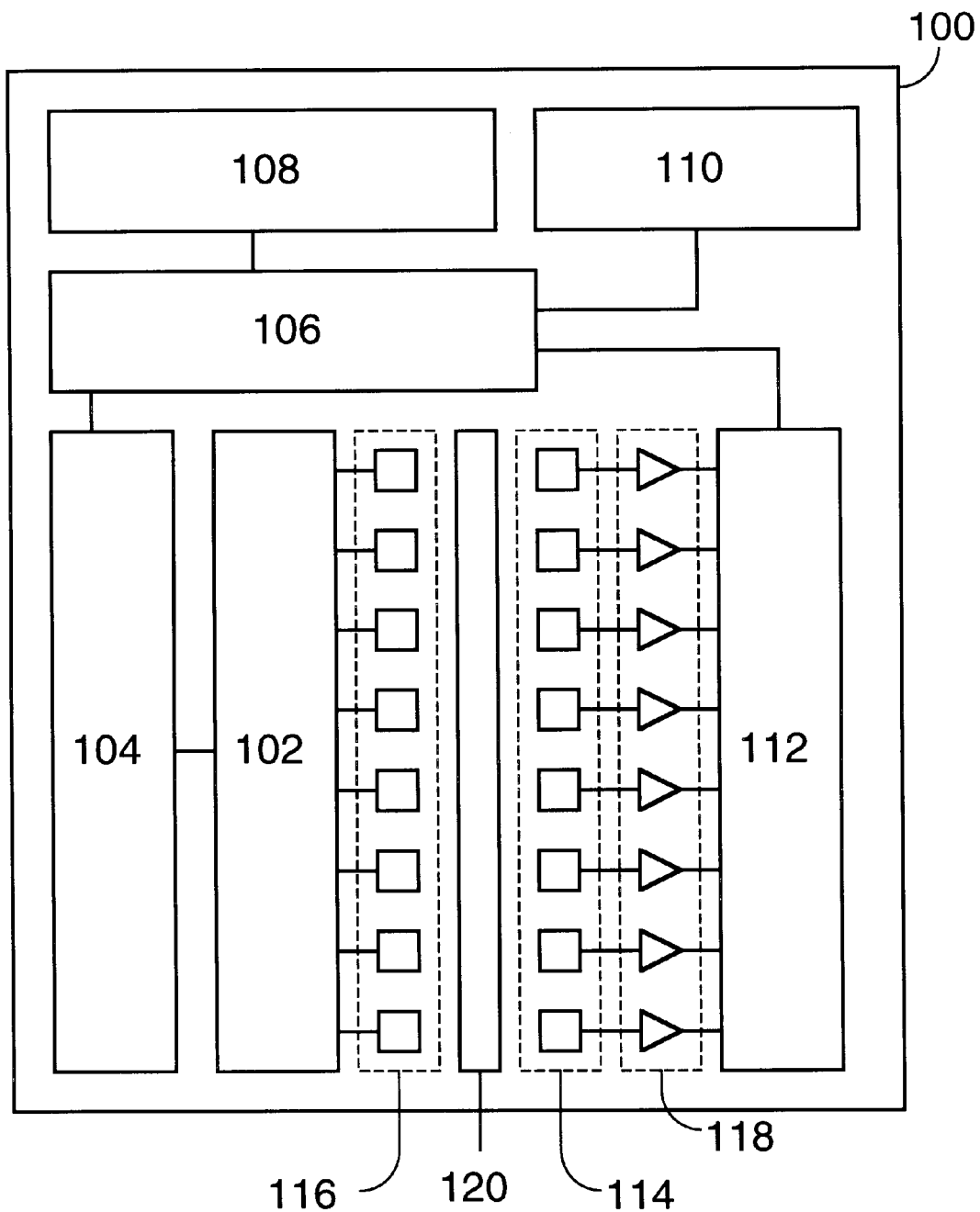
FIG. 6A shows an alternate embodiment of the invention in the form of an application specific integrated circuit (ASIC).

FIG. 6A shows an alternate embodiment of the invention in the form of an application specific integrated circuit (ASIC). A silicon substrate 100 contains integrated circuitry similar to that shown in FIGS. 2B and 2C. Included is an LED multiplexer (or analog switching array) 102 connected to an LED combination and sequence control circuit 104. A digital signal processor (DSP) 106 attached to a memory 108 and clock 110 is used to command LED control circuit 104. A multiplexer and A/D converter circuit 112 receives amplified signals from a detector array 114 and provides digital representations of these signals to DSP 106 for analysis. A collection 116 of LEDs are die attached to pads on the silicon substrate 100 and lead bonded to its bond pad. Note that, alternatively, the LEDs may be integrated into the substrate if the latter is composed of a material whose band gap can be adjusted over the different LED regions. These LEDs are activated by LED driver 102. Similarly, the collection 114 of detectors are connected to respective amplifiers 118 which provide detected signals to multiplexer and A/D converter 112. The entire assembly can be exceedingly small. For example, with 0.015 in. center to center LED spacing the active emission length can be ¼ in. long with a detector width of 0.020 in. and optical barrier widths of 0.010 in. The entire assembled chip can be put into a small SSOP IC package having an optical window on top as small as 0.250 in. long and 0.080 in. wide. The IDEA probe package can have as few as few as 4 leads comprised of (1) power supply, (2) ground, (3) clocking, (4) serial A/D output although other configurations with 8 to 12 leads permits greater circuit flexibility. The silicon detector can be covered with thin glass or quartz windows with a dividing metalized strip 120 to serve as the optical barrier. The LEDs can be covered by a similar glass slab metallized at their joined edges so that the entire package has a glass window in the SSOP IC package. Clear epoxy can be used to cement the glass to the semiconductors. This provides a "spectrometer" in a miniature IC chip package that can be employed as a generalized component with digital in and digital out precision for spectral identification or analysis purposes. By making the metallized edge optical barriers thinner, the detector can approach 0.080 in. wide by 0.250 in. long. A 0.1 in. thick package could then have an edge viewing window with pins emerging from the opposite edge. They could then readily fit between the fingers of a human hand and used to identify pretrained patterns for hands. They could also be used at the tip of a pen or in other example applications discussed herein.

For certain IDEA probe applications the emission spectra of each light source need not be a single narrow spectral band. Similarly, the detectors need not be spectrally flat over the region of re-emissions encountered for the objects being tested. For example, certain classes of LEDs have spectrally broad secondary emission regions at longer wavelengths than their spectral peak. The emitted photons in such regions can readily be 30% of that in the region near the peak. The detector efficiency over that broad spectral region may exceed its efficiency near the spectral peak, such that even 50% of the throughput photons may derive from the secondary peak. Stokes fluorescence and other spectral characteristics of the object can further increase this percentage of emission/detection throughput at the longer wavelengths.

Even with this lack of spectral selectivity, so long as the spectral density characteristics of the emitters and detectors remain invariant over all tested samples, the multivariate analysis method employed can still discriminate object properties. Such multi-band emissions may cause a greater loss in resolution for certain object properties, (for example density of states) than they would for other properties, (for example identifying into which of many classes an object fits by its "color"). For test objects of certain color, (for example a passive GaAs LED die that would exhibit secondary emissions when forward biased) the discrimination of object class may actually be enhanced by a "matching double spectral emission band" in an LED of the IDEA probe being used for discrimination. Thus, with a sufficient number of spectrally different emitting LEDs, constancy of each spectral envelope may be more important than the precise shape of each spectral envelope. This can be exploited as a feature derived through using large RADEL arrays of different LEDs in IDEA probes.

It could for example be used to optically compare emission properties of each LED on a large fab wafer of LEDs in process, prior to lead bonding or electrically contacting to the die on that wafer. In such a case the LED of the IDEA probe might be comprised from a long continuous strip (one LED wide) of unseparated die derived from a wafer which had a gradient in some spectral property for die along the length of that strip. Such an emission strip of lead bonded die used in an IDEA probe employed to irradiate respective un-bonded die on a fab wafer in process of similar shape and composition, when physically moved through consecutive matched and registered die positions, can without electrical contact, enable determination of the relative optical properties of those fab wafer dies. This is an example of how judiciously constructed IDEA probes can be employed to enhance the manufacture of LEDs and other IDEA probes. It is further feasible to design and build wafers of LED die with intentionally enhanced gradients in desired spectral properties along connected die strips, to be so used in IDEA probes.

Figure 6B:
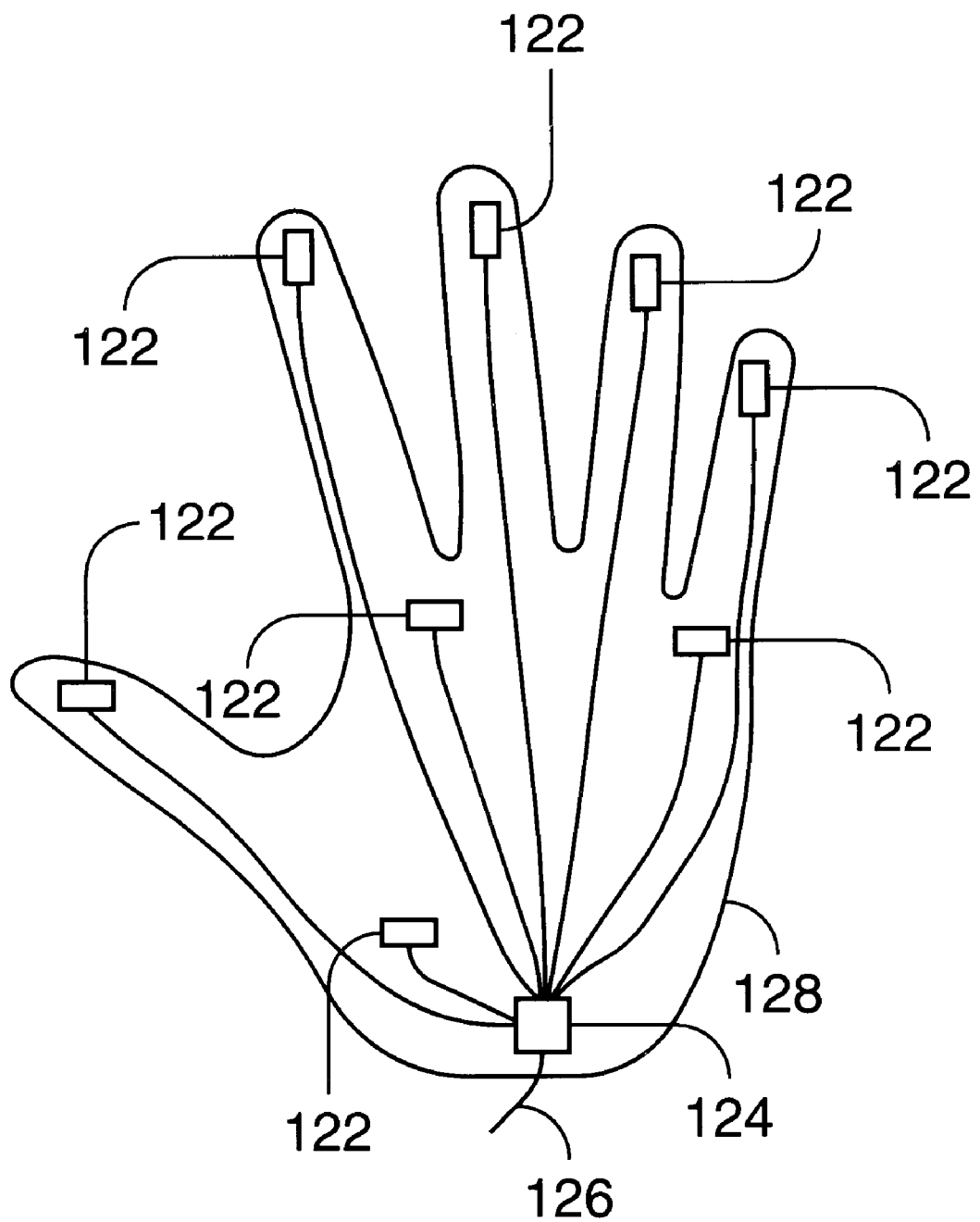
FIG. 6B shows an embodiment with several SSOP IDEA probe packages (as described in FIG. 6A) attached on the fingers and palm of a glove.

As shown in FIG. 6B, a very useful IDEA embodiment involves mounting several SSOP IDEA probe packages 122 (as described in FIG. 6A) on the fingers and palm of a glove 128. The packages 122 are connected to a central control circuit 124 in the glove to supply power, grounds and control signals appropriately interconnecting the packages. From the control circuit is a lead connection 126 to a computer, perhaps located on the back of the hand where it would least interfere with grasping. Infrared or RF coupling is an alternative. In one variation, an independent battery operated glove has a controlling DSP or microcontroller which executes the identification algorithm and provides feedback signals to the glove user (which might be a "mechanical hand" in automation type applications). The glove can be worn for picking/sorting fruit, food, minerals, ore, leather, wood, foam, grasping assembly line parts/objects, etc. As the fingers approach and close upon the object, the probes measure its surface and bulk properties and the system attempts to recognize properties of the object and provide an indication of such to the user. Crosstalk between SSOP packages can be employed as in the embodiment of FIG. 4B. In liquid, gas, or powder mediums objects could be identified by grasping, even though they may not be clearly visible to the eye due to turbidity or lack of light. Position sensing mechanisms in the glove could also monitor finger closure indicating the position of the hand for virtual reality type applications. A pair of gloves can be used for differential comparisons of symmetrical body parts or different regions of an extended object.

In addition to an IDEA probe approaching and touching the unknown surface, it can be moved across the surface of the object (either at a small distance or while touching the object) to scan differing regions of the object. This can effectively generate a low resolution N color picture of the object derived from data at and/or just below its surface. In simplest linear form with only one LED of each wavelength forming a line, "raster" lines sampling N wavelengths along parallel adjacent lines comprise the final image. Such characterization is useful to identify patterns slightly under the unknown's surface, and whose depth and nature may be obscured by surface patterns. Example uses of such a probe which can provide images, however crude, below a surface within a turbid material include the characterization of paintings, printing, artwork, substrates, identification of subcutaneous biological disorders, analysis of materials having striations like plants, minerals, textiles, tiles, cardboard, and wood. The image generating properties of a sequentially driven linear RADEL array using even a single detector are seen to form a dual analogy for image generation to a linear PIXEL array using even a single light source. This analogy between the arrays also extends to integrated structures where, for example, all different wavelength LEDs would constitute luminescent diodes of slightly varying emission wavelengths on one single semiconductor die fabricated using semiconductor photolithographic techniques and bandgap modifying "alloys". This could be used in the ASIC of FIG. 6A.

Another embodiment analyzes color changes in small loosely adhesive gel strip electrodes worn against the skin with IDEA probes sensing the optical filtering or color change of the gel caused by an externally applied electrical current between strip pairs. The applied current brings subcutaneous ionic and non-ionic molecules osmotically outward through the skin onto the gel electrodes and the resulting photochemical reaction thereby alters each gel wavelength transmission or retroreflection properties as seen by each respective IDEA probe looking through each gel strip toward the skin. Temperature and ultrasonic signals applied to the skin can be used to modify and control the transdermal transmission of ions and molecules through the skin either way. The 15 (or whatever necessary) different wavelength throughput variables per probe are fed to a discrimination algorithm which identifies one or more specific subcutaneous constituents (or percentage thereof) associated possibly by pretraining with a given regime of applied current, which can be varied in time, magnitude, and direction. There is generally a transdermal molecular weight cutoff. Each gel strip and probe can be placed on any external portion of the body granting different skin thickness, transmissions, and cutoffs. These generally require an electronically controllable current source and ultrasonic source between anode and cathode gel pairs programmed to maximize the desired coloration differences that associate with the presence of whatever constituents is being identified. The gel strip electrodes generally contain silver/silver chloride and may also contain chemical reagents transmitted inward through the skin to the tissue to produce subcutaneous reactions that enhance exterior coloration effects in the gels. Besides transdermal iontophoretic transfer of molecules, chemicals and constituents can pass or get dragged inward or outward by ions migrating through sweat glands or hair follicles to create the necessary color changes. Integration times may require from minutes to hours depending upon reagents and the identified constituents. Heat, cold or pressure applied at the electrodes can be used to modify coloration effects and add further discrimination.

The configuration can be attached semi-permanently or for noninvasively monitoring a patient in a hospital bed 24 hours per day, or worn as a portable wrist or waist band. By placing gel electrodes between symmetric body positions, asymmetries in the presence of subcutaneous constituents can be detected.

A significant advantage of IDEA probe discriminators at anodic/cathodic electrode sites in transdermal osmosis is the ability to analyze the N dimensional data (of N colors) resulting at each site in the pair (as compared to just a current or voltage). The differing resultant spectra at each site, and between both sites of a pair positioned at different body locations permits extracting discrimination information through: spectral analysis, differential spectral comparisons between both sites, differential transdermal permeability at different body locations, differential subcutaneous constituents located at different body positions, differential anodic and cathodic effects that are electrically and ultrasonically controllable. The algorithm can thereby identify via throughput variables of the IDEA probes, both charged analytes which migrate from the prevailing field plus non-analytes dragged along, plus those due to intrinsic body reactions and reagent induced reactions.

Figure 7:
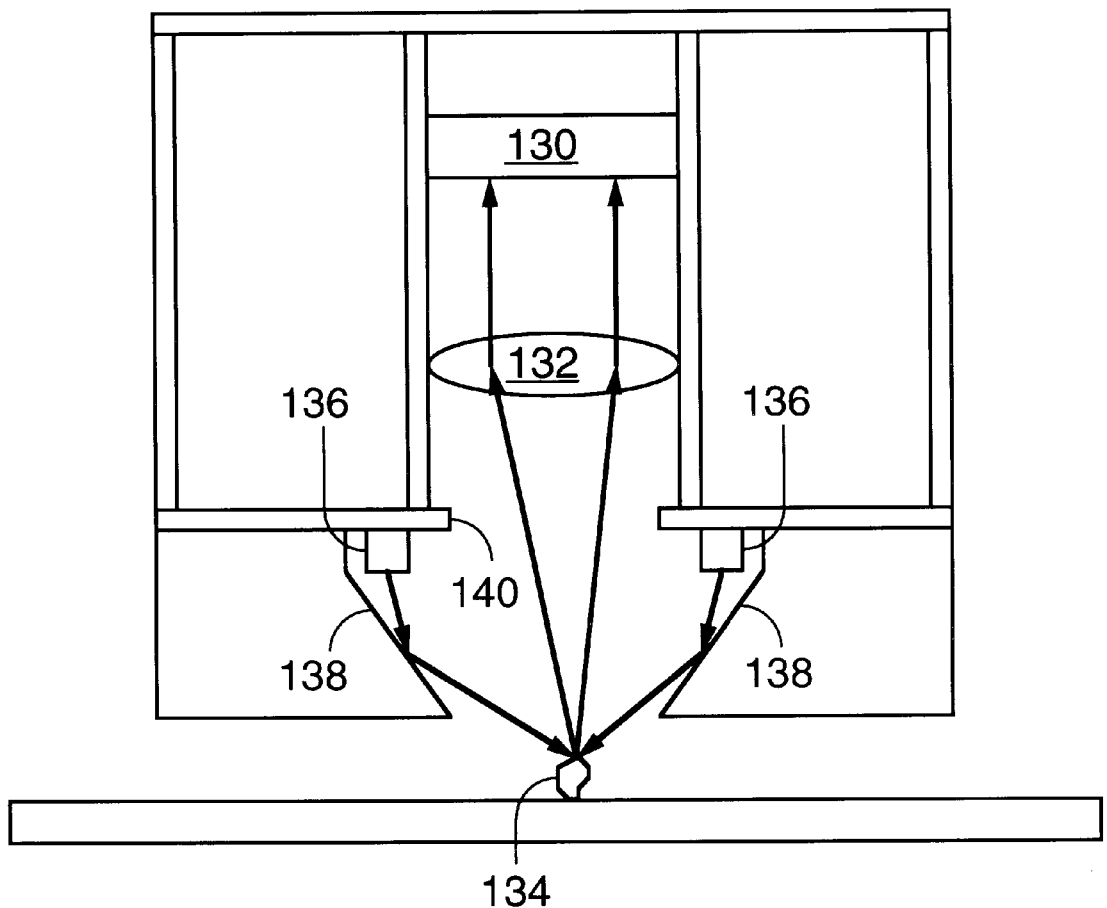
FIG. 7 is a cross-sectional view of an embodiment of an IDEA probe having a CCD array to form a probe detector with many thousands of detector pixels.

FIG. 7 is a cross-sectional view of an embodiment of an IDEA probe having a CCD array 130 in place of the detectors of FIG. 2C to form a probe detector with many thousands of detector pixels. An imaging lens 132 is positioned to focus the light from an object 134 upon the array 130. An aperture 140 serves as an optical barrier. A ring of LEDs 136 are positioned in conjunction with reflective surfaces 138 to illuminate the object 134 with independently controlled multiple wavelengths of light. In one mode of operation one or more LEDs 136 are actuated for each full frame (or several) of the CCD array and different LEDs may be actuated for consecutive frames in sequence. We call the interval associated with each such full picture frame an image-frame interval and each such frame an image-frame. In another mode devised to ascertain physical properties of the object associated with relative movement, many LEDs are actuated in sequence per image frame interval. For ordinary TV an image frame interval often corresponds to the period of two cycles of the power line frequency. Under control of the signal processor, or under manual control, the system may switch from operating semi-continuously under one mode, to operating under the other mode, and then back. Materials brought into the focal plane of the lens system are sequentially illuminated by the ring of LEDs which surround the focal surface and face the test object. Here primarily surface reflectance properties are measured as in a microscope. The acronym CCD is used in the present description to include any dense detector array device that collects optical data, such as charge coupled devices, CMOS imaging chips, CID arrays, solid state video and still cameras, whether or not conventional images derive from such use.

Figure 8:
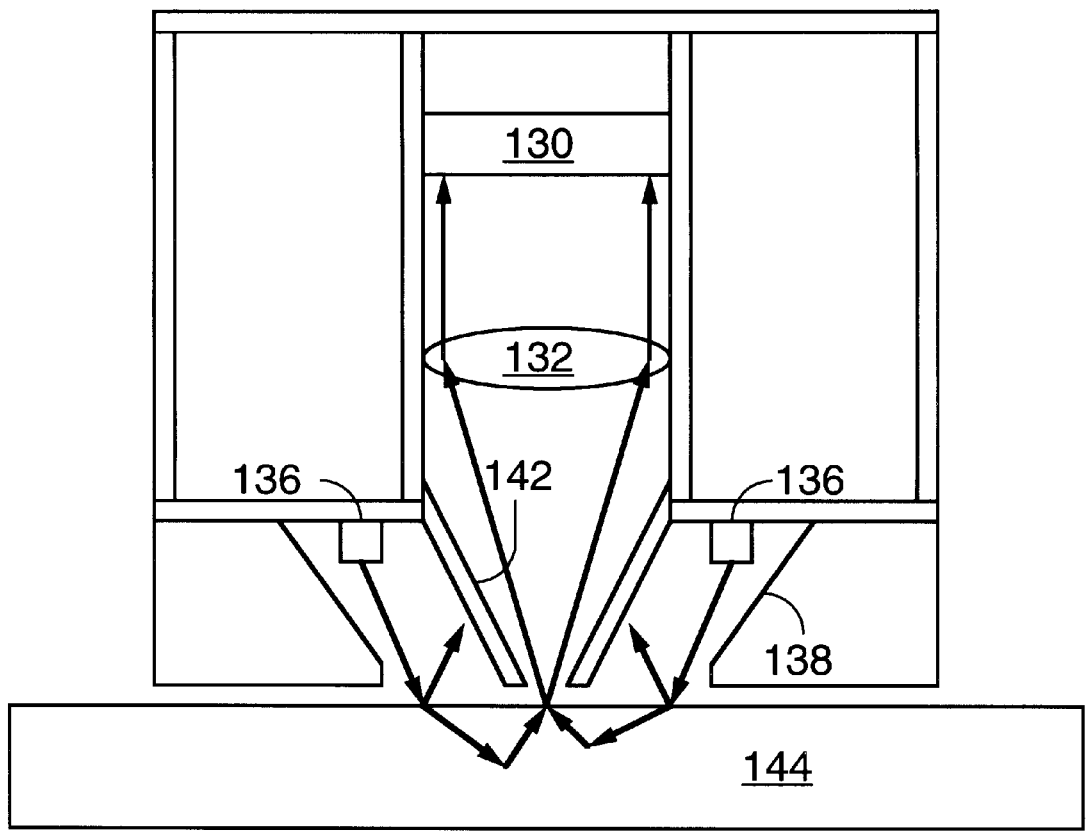
FIG. 8 is a cross-sectional view of a variation on the embodiment shown in FIG. 7.

FIG. 8 is a cross-sectional view of a variation on the embodiment shown in FIG. 7. The apparatus is designed to enhance measurement of properties within the subsurface of a material 144 by forming the optical barrier as a tubular or conic ring 142. The probe can be brought to and from the surface as discussed in reference to FIGS. 1A and 1B. The optical barrier 142 can be made detachable if it is desired to examine the optical surface at close proximity without subsurface information. When the IDEA probe with optical barrier is brought from far away toward contacting the material surface, the camera image progresses from an out of focus blur of a large area to a progressively smaller central region with continuously improved resolution. When the probe is in contact with the surface, the circular periphery of the image receives greatest illumination, which illumination is solely through subsurface scattering/transmission. With the camera image plane set just below the surface, the image shows the absorption/scattering/transmission profile varying radially in intensity with the degree of graded illumination increasing outward from the darker center. The image can also indicate any non-radial asymmetry and optical anomalous regions within the subsurface field of view appearing as darkened absorptions or brightened scattering along the paths of illumination.

Since a relatively sharp image of the surface would be derived just prior to contact, that image can be used to at least partially subtract out surface obstructions of the subsurface. This includes, for example, algorithmic "subtracting out" of surface hair, scuff marks, scratches, abrasions, creases, parasite clusters such as moss or lichen, weathering or even thin surface coatings like paint and patinas. At the outer periphery of the image the illumination angle changes rapidly just prior to contact and thus this annular ring region of the image provides a "scan" of the different angular illuminations of the surface. Various such acquired properties can be algorithmically manipulated to enhance the extraction of features and identifications about that region of the image.

Figure 9:
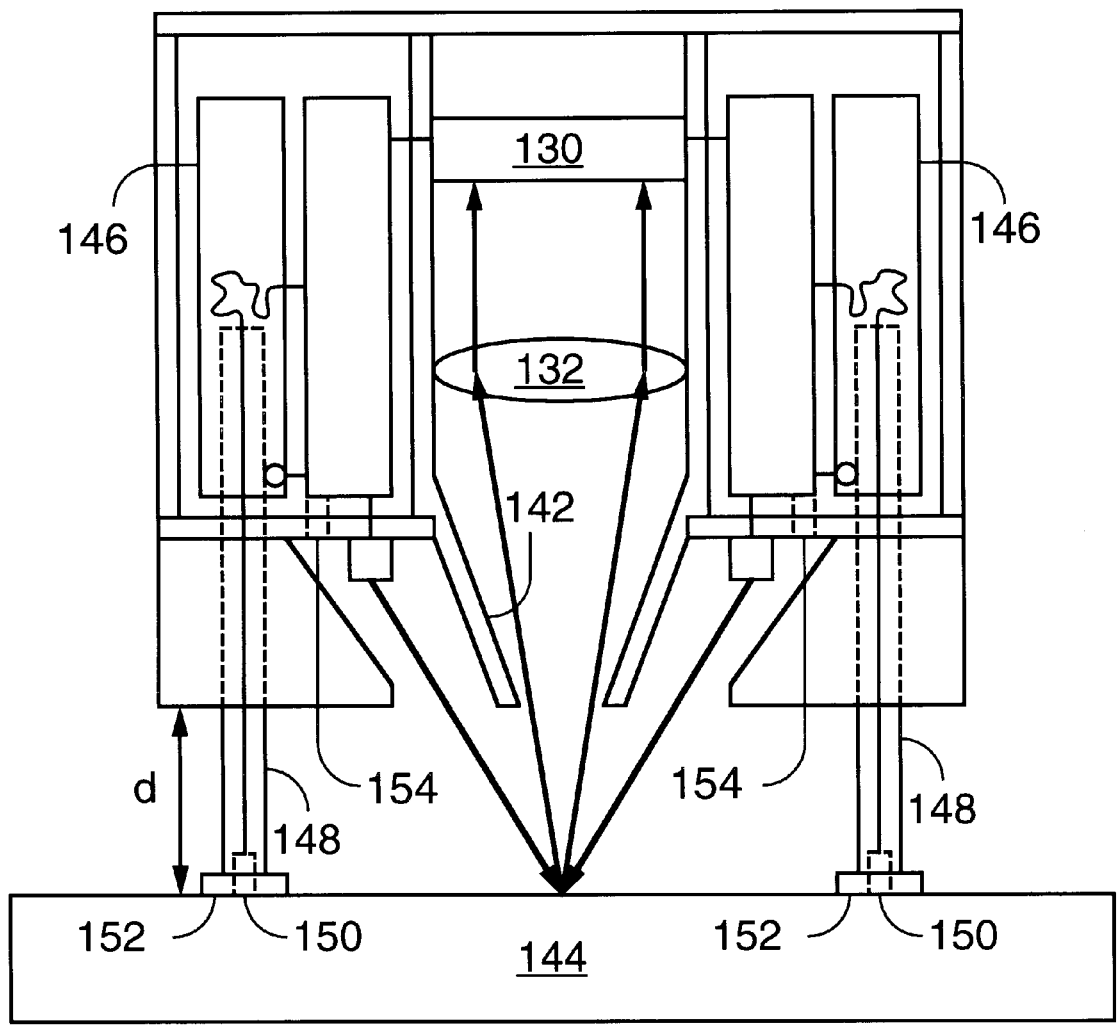
FIG. 9 is a cross-sectional view of another embodiment illustrating various possible enhancements to the probe of FIG. 8.

FIG. 9 is a cross-sectional view of another embodiment illustrating various possible enhancements to the probe of FIG. 8. This embodiment includes a linear displacement controller and/or sensor 146 that electrically adjusts and/or measures the distance d between the probe and the surface as determined by the position of movable legs 148. The distance d can be provided as a variable to the processor for inclusion within the analysis and identification algorithm. With four independently controlled legs the tilt angle can be registered for gross angle measurements. An enhancement includes circuitry and mechanisms to couple the distance d to automatic lens focus adjustment such that the focal plane is controlled as a function of distance d. In another variation, electrodes 150 can be provided at the feet 152 of the legs 148 to enable the measurement of electrical skin resistance and other similarly determined physical attributes of the object 144. These attributes can be used to supplement and enhance material property identification. In another variation, the device may be provided with gaseous sensors 154 for sensing gasses, ions, and airborne particles which may also be used to supplement and enhance material property identification. As these examples illustrate, any physical detector or sensor may be integrated within a basic IDEA probe to enhance its functionality as needed. Conversely, an IDEA probe can be combined with or integrated within known sensors or sensing techniques to provide improved identification or measurement of material properties. Note that the apparatus may be provided with a tubular shroud to reduce the effects of background illumination of the material.

In a RADEL array, for each specific LED wavelength, two, three, or Q (same wavelength) LEDs can be located at symmetrical radial positions to attain any desired degree of side shadowing, back lighting, and ring-lighting in the camera image, depending on whether the Q same wavelength LEDs are separately or simultaneously actuated. There would then be 2N or 3N or QN LEDs around the ring.

In addition to up to Q consecutive sequences taken to provide shadowing at each identical wavelength N, those N consecutively different wavelength illuminations effectively generate an N color frame-sequence camera with "colors" obtainable into the infrared and having electronically selective shadowing. The number of significantly different wavelength LEDs currently available now approximates 40 and the inventors have reduced to practice such systems with N=15. Since all pixel elements of a broad spectrum band CCD (otherwise called a black and white CCD) occupy identical physical locations for the different LED illuminations, for small region and macro imaging the performance of this configuration exceeds the highest quality studio-type 3 color separation RGB television camera. Each "color" of the image occupies precisely the identical pixel topology without mirrors, filters or registration difficulties. Additionally N colors are now possible instead of 3 colors while requiring only one "black and white" CCD array, which generally can be more sensitive, more stable and having each pixel shape and area optimized and precisely invariant in image position for each wavelength illumination.

For example with a ½ in. square CCD matrix array of one million pixels each pixel retains precisely the same (maximized) area for each color change and remains in precisely the same position for the N cases of illumination. Such exact registration is extremely important for pattern recognition of the N color images. This provides the equivalent of N identical perfectly registered CCD arrays illuminated through N spectrally selected mirrors. For material identification through instruments the problem is radiometric, rather than photometric as pertains to vision through the human eye. Wide spectral bandwidths as with red, green, and blue tristimulus curves are not particularly desirable for identifications because the output is proportional to the integrated area under each curve and provides an average over a broad spectral region rather than over narrow selective regions. It is preferable to use many "discrete colors" each of narrow bandwidth. Narrow spectral bandwidth measurements minimize or avoid integration errors which, under broad spectral detection curves, can yield identical integrals for any incoming radiation weighted in intensity by the inverse of the spectral curve. These are analogous to the ambiguities associated with metameric colors. For conventional TV timing each LED can be on for $\frac{1}{60}$ or $\frac{1}{30}$ sec to provide N=15 different color images per total frame sequence comprising ½ or ¼ seconds; or much faster if desired.

It is sometimes desirable or necessary to put an optical filter over certain of the LEDs or detectors to 1) Reduce the effect of secondary IR radiation from the LED. 2) Make specific detectors wavelength-sensitive to fluorescence or to radiation arriving from different directions (angles), as with interference filters. This can be achieved in several ways. Liquid coatings, analogous to gelatin, which harden into gelatin-like optical filters can be placed over specific LEDs or detectors by conventional die coating apparatus whose outputs are location controllable. A pick and place machine (that employs vacuum pickup of die for example) can pick up small diced-up interference or other filters and judiciously place them on top respective detector or LED die that are freshly coated with clear epoxy, or other suitable thick coating. These are placed such that the filters are epoxied just above the lead bond wire connected to each respective die. A third method entails pre-placing the cut-filter dice onto an epoxy coated glass or plastic substrate strip in accord with where they are desired to end up bonded to the strip. The entire substrate strip having different filters in different areas is then placed atop the freshly epoxy coated sub-assembled LEDs (or detectors) with filters in their respectively needed positions. The epoxy then bonds all filters on the substrate into the final position necessary for optically filtering the radiation.

It is sometimes desirable to coat portions of the object under test with liquid crystal material, or any material that changes color with attributes of temperature, pressure, stress, strain, illumination, electric or magnetic field, current, vibration, motion, ions, chemical environment, or metabolic activity. This allows any such respective localized attribute variations of the object to be conveyed to the detectors and signal processor, and they enable enhanced identification of its properties.

Figure 10:
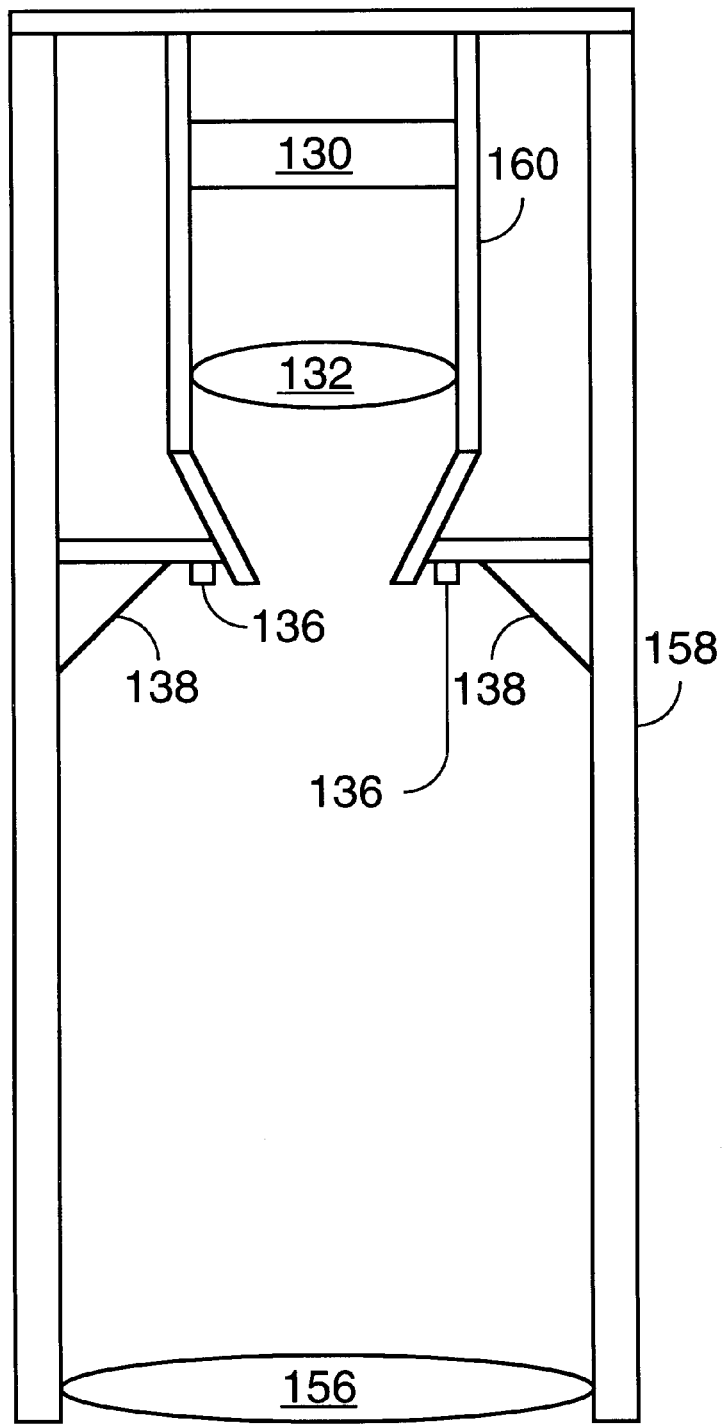
FIG. 10 is a cross-sectional view of an embodiment of an IDEA probe which provides a "flashlight" type probe for the sensing and identification of remote objects.

FIG. 10 is a cross-sectional view of another embodiment of an IDEA probe which provides a "flashlight" type probe for the sensing and identification of remote objects. A probe similar to that of FIG. 7 is provided with an additional lens 156 mounted near the end of a tubular housing 158. The detector 130 in this case might be a photomultiplier for high sensitivity configurations or a CCD detector as just described, a PIN detector, or an avalanche detector. The detector is surrounded by a thin tubular wall 160, and an optical barrier aperture 140 is provided to prevent close proximity crosstalk from the LEDs 136 to the detector 130. The lenses 132 and 156 project the image of the RADEL/pixel assembly 130 far away or toward infinity. The lens 132 close to the CCD array is not necessary if the array 130 and LEDs 136 are within almost the same plane. For a 3 in. lens 156, about 0.5 steradian of the LED's radiation will emanate in about a 2 degree diverging beam. Whatever object comes into the field of view and intercepts the beam, some fraction of its reflected illumination will be recaptured by the lens 156 and land on the central region detector. The relative values of the differing OSVs (here with M=1 for a photomultiplier or single detector, and M=~$10^6$ for a CCD array) will give indication about the reflected spectral properties of the passing surface. Similar reflected signals will result if instead of hitting an object's surface the beam traverses opaque or turbid droplets, liquid, gas or dust in the air.

Thus, some indication of the spectral properties of the objects along a "flashlight beam" can be ascertained in real time. If the object is made to traverse the field of view at the image plane, the NM detected signals over repeated frames relate to the M spatial characteristics of surface reflectivity of the object at each wavelength. With the IDEA probe set at a fixed focal distance in a production line photosensor setup, identification of the passing product, and its spectral and temporal properties can be ascertained. When the single photomultiplier or photodiode is replaced by an M element CCD array, the object's spatial/temporal orientation and radiometric properties can be obtained in the form of a dynamic image. Emitter-detector crosstalk from the reflections off the flashlight lens can be minimized by using a meniscus lens and subtracting out each fixed crosstalk in the absence of an object in the field of view.

Figure 11:
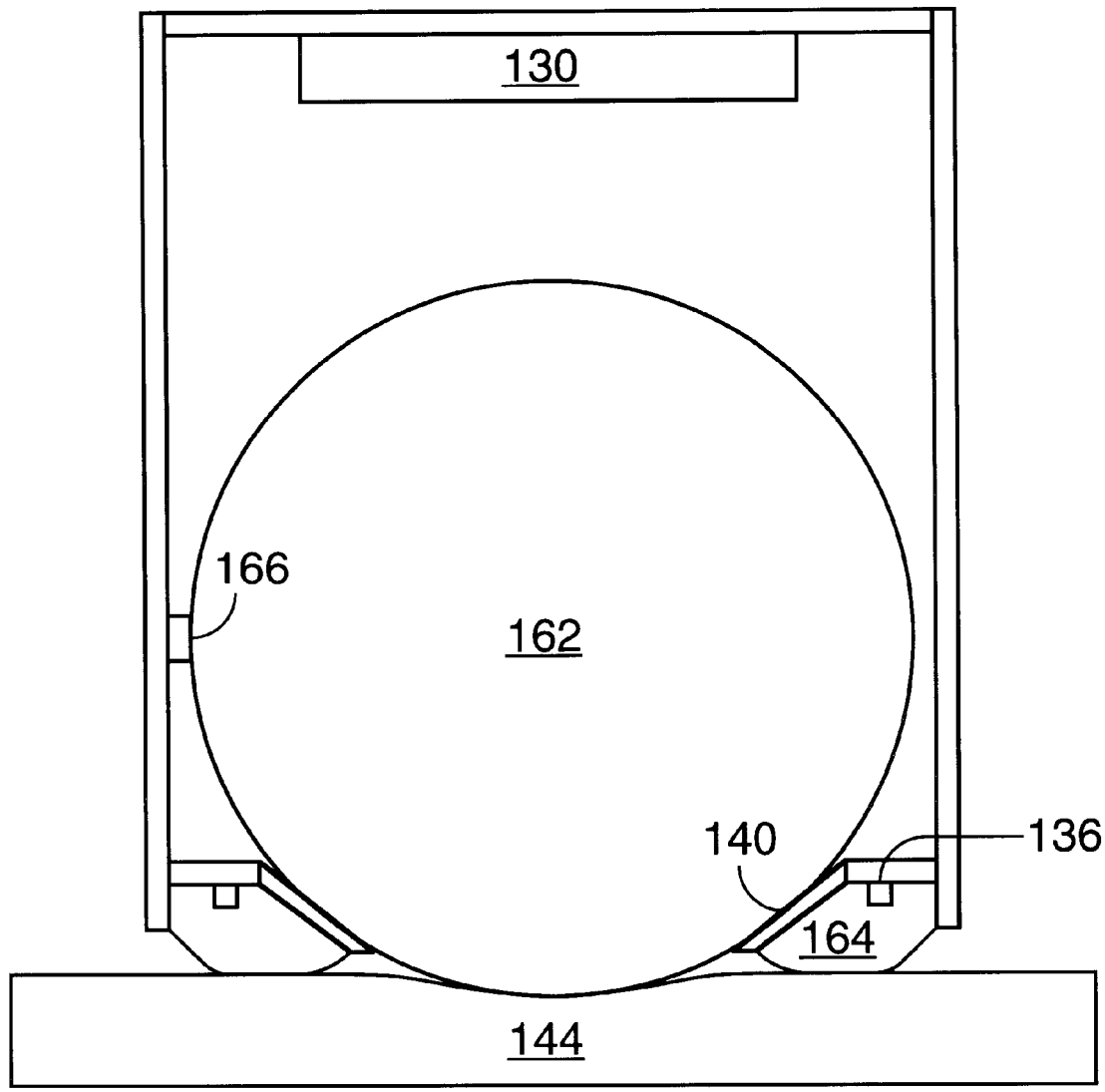
FIG. 11 is a cross-sectional view of an embodiment of the invention which makes use of a spherical lens which may roll over the surface of the object, or be fixed.

FIG. 11 is a cross-sectional view of a particularly useful embodiment of the invention which makes use of a spherical lens 162 which may roll over the surface of the object 144, or be fixed. Lens 162 may be, for example, a clear marble sphere about 1.5 to 4 times the diameter of the ring of LEDs 136. The focal plane of the detector array 130 can be slightly within the material 144 when the marble is in contact with the material surface. Lens pincushion effects can be reduced or eliminated by computer processing of the image and utilizing the central most region of the image. The material's surface reflections are also minimized because of the steep angle at which light from the LEDs can be made to impinge on the surface over the field of view. In effect this system forms an N color "microscope" type image whose image plane can be adjusted above or below the material's surface.

Geologists, for example, often view minerals through a clear flat glass illuminated at an oblique angle. A clear "oil" pre-applied between the glass and mineral minimizes the optical dielectric interface between them and permits greater clarity of conditions immediately below the mineral surface. Generally, illumination derives from an incandescent lamp. Such an apparatus can be replaced by an IDEA probe according to this embodiment. The viewing can be on a computer screen using any desired false coloration algorithm and the computer can composite larger areas scanned from the sum of scanned smaller ones as the ball lens moves over the surface. Thus high resolution large area, spectroradiometric images can be acquired, viewed and computer analyzed to identify characteristics of the materials. The illumination wavelength spectra can derive from any combination of the N LEDs.

Several means can be employed to reduce blurring of the subsurface image due to scattering. One such method uses time-of-flight gating. The LEDs and detector must have very fast rise and decay times (in the picosecond range) or be modulated at relatively high frequencies. Another method involves polarization difference imaging utilizing pairs of same wavelength LEDs with each alternate one (A and B) having its output polarized orthogonally by an intervening polarizing filter. Each pair of adjacent LEDs of the same wavelength A, then B, consecutively irradiate the material with orthogonal polarization. In front of the CCD array is a synchronized liquid crystal polarizer/analyzer (or an electronically controllable birefringence analyzer system). Then, polarized components of each image received can be compared digitally as A+B or A−B and affine transformations between the derived images can produce an image with significantly reduced blur from scattering within the material.

A third method of reducing the effects of scattering within the image bears some analogy to synthetic aperture radar. It requires that the light source and detector array move in a definable way relative to the object. The images so derived are correlated to reduce obscurations due to scattering. The embodiment is essentially as shown in FIG. 11 except that the clear spherical lens can rotate against the test material surface as the probe moves, similar to a large ball point pen. The ring of LEDs and metal reflector/optical barrier are located so as to give sufficient clearance in order not to obstruct the "ball pen" type motion against the material. Clear epoxy 164 both protects the LEDs 136 and provides a smooth contact surface with the object 144. A pickup mechanism 166 detects the ball motion which we will assume for discussion here as limited (by a central axis through the ball if necessary) to only rotate in the X (or Y), orientation of pixels on the CCD. Other ball positioning methods can also be employed, as in a computer mouse, or by sensing encoded reticles on the ball, or computer pattern recognition of the changing image positions on the CCD which could then recognize both X and Y orientations simultaneously. In this manner motion of the "ball pen" corresponding with the image region's traversal of each line of pixels in the CCD array is electronically registerable. This is also achievable via image processing software which morphologically tracks each portion of the image as the pen moves. By digitally processing the changing image produced as the probe moves, the computer algorithm can discern each consecutively adjacent row of pixels recognizing each such row to depict the same fixed line position on the image, which it will indeed represent with proper registration of the ball rotation. Imagine a hair on the surface of the skin being in the image as the ball progresses. As the image of the field of view moves across the CCD pixel plane, row-by-row, the algorithm can "track" the relative position within the material from which each consecutive line of pixels encountered must have originated in the test material. The computer can track the hair as reference. The result is that the computer can interpret the source illumination as being different for each such consecutive line of pixels traversed, though the respective scene objects being scrutinized within the material will be the same, just shifted in position. The result would be like strobing the scene with an illumination source that moves linearly through P different positions where P is the number of pixel lines in the X (or Y, or both) direction(s). Having P linearly staggered angles and shadowed illuminations of each pixel line of a scene is better than having a single illumination of each line of a scene in terms of shading and being able to algorithmically extract information about the scene. Material identifications and subsurface property determinations can be enhanced compared to an image formed from simple fixed illumination. These configurations allow physical properties related to the inhomogeneous morphology of objects and materials to be measured.

Another advantage of using pulsed monochromatic sources vs. spectrally decomposed broadband sources with filters, prisms or gratings involves the "sharpness" of the image obtainable for video or still frames. Though CCD detectors, for example, integrate the impinging photons in the form of stored charge, there is always some loss or smearing due to charge recombination during the interval of scanning out a raster line of pixel charges under prevailing illumination which creates scanning image blur. The illumination is not removed while scanning out the data. Each pixel element does not act as a perfect capacitor but as a lossy capacitor. For a fixed total number of integrated photons in a pulse the effect of this loss can be reduced by increasing the N photons arriving in a shorter pulse. An analogous non-reciprocity effect occurs in a film at low levels. Accordingly, "strobing" the illumination for each consecutive frame of a TV or movie camera can reduce blur from non-reciprocity effects, for fields-of-view which are changing, and during data shift-out. The use of a shutter becomes unnecessary for shifting out a raster line of pixel charges. It is generally not feasible to analogously increase the photon arrival rate into a shorter pulse for spectrally decomposed broadband sources without greatly shortening of the source life. Such sources are also not linearly related in current (or voltage) applied and photons/sec per spectral interval. Also the depth of optical penetration at which the illumination level compares to the background noise level can be deeper for a short high intensity pulse.

Further advantages of this embodiment are as follows. A lubrication "clear" fluid can surround the ball and be deposited upon the test material in direct analogy to a ball-point pen. This can minimize the optical dielectric interface between the test material and the ball and between the ball and CCD arrays. That enhances the extraction of images below the surface when the focal plane of the system is below the surface. An immersion lens system is formed without the messiness of preplacing oil over the regions to be scanned. The lens is also a dispenser. Adjusting the height of the CCD permits varying the depth of the image from "virtually at" the surface, to deeper within the surface. The steep angle of LED illumination reduces surface reflections that could otherwise dominate the resultant image. The illuminated image plane receives primarily scattered light coming in peripherally. While this might not provide uniform illumination over the field of view it allows examination of the test material under a gradient of illumination in the radial direction. By moving the probe over the material surface any specific region will traverse the highest to the lowest illumination and the differing scattering patterns so derived en route can further be algorithmically useful for discrimination.

It is also possible to put chemical sensitizers, dyes, fluorescing, phosphorescing reactive agents, antigens and specific attractors into the fluid to enhance the specific detection of select substances. These can be preselected to promote detection via fluorescence, phosphorescence, chemical, mineral, or biota or viral presence, adsorption of material, thermal conditions or pressure. Moreover the ball fluid leaves a 'trail', literally the marking of the "ball-point pen", to establish precisely what region was examined. Thus for example a physician wishing to examine in detail the image of a vein or artery below the skin surface might trace the "pen" probe along the vein while examining the resultant computer image. This trace might be 6 inches to a foot long with thousands of computer enhanced images along the way. A photograph or image of the exact course taken by the probe is subsequently available along with detailed subsurface images. Alternatively, the physician might be examining scar tissue from an old laceration that has lost surface visibility in places, and a computer might analyze the healing process via the image. Because tissue penetration depths in the near infrared can approach a centimeter the acquisition of crude but otherwise unattainable images of biological networks is feasible. Of course scattering effects at depths of a cm. would not permit sharp images in tissue but particularly in conjunction with the other wavelength images, some identifying features are possible approaching this depth, particularly with an infrared CCD detector array. Again a key assembly element in this IDEA probe embodiment is the same fabricated ring multi LED array as discussed for the other ring embodiments.

A further means to algorithmically enhance subsurface image quality in such identifications is through the application of an external parameter to which portions of the image may be sensitive. Examples methods using such parameters include application of electrical and magnetic fields, heat, cold, pressure (force), and time (relaxation time). One medical example prevails for the ball pen IDEA probe from pressure effects on subcutaneous tissue. Below the ball, blood flow to the area can be diminished due to pressure during the interval the ball traverses each region. (This effect is observable by pressing with a finger for several seconds on nearly any region of the body and noting that immediately upon pressure release that area is less red than its surroundings. Blood flow from the arteries has been restricted by the pressure.) As the ball progresses along the skin slowly and with appropriate pressure, the imaged area defined by the leading edge of pixels initially experiences conditions of normal blood flow while blood has become significantly restricted to that same area by the time the ball approaches its trailing edge of motion. Thus each line of pixels in the image becomes "modulated" by what one might call a "wave" of the absence of blood that traverses the image. Since red blood cells are one of the main optical scatters in tissue, an algorithm can deduce (1) properties and crude images of the blood itself not otherwise discernible by ordinary techniques, by at least partially excluding by algorithmic subtraction the surrounding tissue, (2) properties of the tissue itself without blood and not otherwise discernible through ordinary techniques. The pen probe need not move rapidly as in writing, but can progress slowly along any channel-like structure. Spiral trajectories are also possible for mapping larger areas in the form of a reconstructed composite overlapping spiral image. If the pressure is applied in discrete increments the overshoot effect of more blood flowing into the region (after it was depleted) than would normally be there can be utilized. Also differential pairs of such IDEA probes spaced a fixed distance apart sideways or ahead/behind can be used to evaluate the cardiovascular recovery properties of the tissue in each region through spectral/spatial/temporal waveshape comparisons of the different components in different or symmetrically compared body regions.

Effects as exemplified above using pressure can analogously be implemented using heat or cold through control of the ball temperature. Also, to the extent the applied fluid is devised to cause a reaction with the tissue under observation, a "wave" of effects of that reaction can similarly pass through the image as with pressure and temperature above, electric and magnetic fields can be spatially imposed near any region of the advancing probe and create discernible reactions on materials, which reaction can enhance discriminating information content in the resultant image. Differing reaction time constants of different cells or organs within biological matter provides another parameter that can help extract image details. Any combination of these externally applicable parameters is potentially useful for image discrimination and that applies for other objects and materials as well as biological matter and tissue, for example in hematoma detection. Preferably, as many different phenomenological mechanisms as feasible and/or practical be used in discriminating different materials. These mechanisms can be interactive or totally orthogonal and each provides additional discrimination variables.

The more independent physical parameters which are measured, the better the identification can be. Consider two totally independent (uncorrelated) phenomenological processes. When the predictability of each process provides discrimination indicating a likelihood of 90% validity, 10% invalid likelihood, the predictability of an invalid result for both in combination would be 10%×10%=1%. A valid result would be 99% likely. If the two processes are not independent (not orthogonal) but say 100% correlated the two processes have a combined discrimination equivalent to only one process and a valid result would be 90% likely. If the two processes are say 80% correlated the combined predictability of an invalid result would approximate 10%×0.8=8% and a valid result would be 92% likely. Accordingly, relative interdependence (correlation) between the sets of variables comprising a multiplicity of separate phenomenological processes generally diminishes their discrimination predictability. Because the throughputs from two separate Radel/Pixel channels in close proximity spectrally in frequency and spatially in distance are typically highly correlated, the second channel does not add a great deal of discrimination capability to the first channel. That is why many throughputs channels are desired with moderate to wide spacing between them in wavelength and spatial distances. For identifications where conditions change dynamically in time, temporal spacings in the measurement of variables can analogously add discrimination capability.

Alternatively, if the ball compartment is fabricated so as to permit a small degree of vertical displacement with pressure, then pressure increases will shift the ball's relative imaging position and the depth of the focal plane within the tissue (or material). Sensing the pressure provides algorithmic information on the location of the focal plane and gives another image discriminant useful for three dimensional computer interpretation. The ball can also be vibrated vertically to induce such phenomena. Also, as described in the earlier embodiments, different image depths, surface and bulk optical properties of the tissue (or material) are algorithmically separable through signal changes occurring during the approach and exit from the surface.

It is noteworthy that using two or more independent discriminate processes (like mechanical and optical here) can significantly improve the precision of identification. The inclusion of other parameters comprising a second (or third or fourth) independent discrimination means is an inferred aspect of each embodiment described herein. The use of pressure to produce a wave of blood constriction progressing through the image is one example of this means.

In general, pattern recognition algorithms that operate on images derived from XY pixel arrays or from discrete detector signals can function with improved efficacy using the kind of spectral, spatial and temporal information attainable through RADEL excitation. Such systems require stable repeatable illumination, defined in wavelength, position and time such as that obtainable from fixed geometry sequenced LEDs. Algorithms can provide most identification analysis via virtually any functional interdependence of spatial, spectral and temporal variables derived from each RADEL/PIXEL channel of the image, (including ambient background). By appropriately interrelating associations of RADEL/PIXEL variables of this type, algorithmic image processing is feasible for digital images in general but with N separate wavelengths. As previously described the ambient background can be canceled out by subtracting from each LED-on-reading that respective pixel output value most closely adjacent in time when all LEDs are off.

The ability to sample instanteneous LED on-voltages associated with respective photodetector signals permits a highly accurate measurement of optical signature properties because LED photon outputs at known constant currents, measured voltages and inferred temperatures can accurately reproduce optical outputs that have been previously calibrated and stored in a memory of the probe or of a computer attached to the probe. Such compensation for instantaneous LED photon output at a known current and measured voltage can be achieved by measuring LED outputs and voltages at two or more known currents and temperatures and by then interpolating and extrapolating (photon output, or throughput for an optical standard) for voltages measured throughout the region. Alternatively the exponential voltage-current law and series spreading resistance of the LED junction can also be applied for temperature/photon output correction.

Consider an exemplary case for discussion purposes, where the 16 LEDs of an IDEA probe illuminator, which, when all activated together would comprise "white light" from blue into the near IR. region. In darkness, suppose those LEDs are illuminating TV frames of an RGB CCD camera with an otherwise stationary image, but having one moving white spot across the field of view. If all LEDs were continuously on during the 33.3 milliseconds of each non-interlaced frame, the image derived would show a "white" streak representing the distance moved in 33 milliseconds as illuminated with "white" light. The image and white streak would be similar to when conventional white incandescent light were used because the sum of all LEDs would be similar to white.

Now instead of illuminating all 16 LEDs simultaneously during the entire frame, suppose that the LEDs are consecutively illuminated for 2.08 milliseconds each, (say 2 milliseconds for simplicity), so that 16 of them coincide with the 33 ms of the camera frame. A multicolor "rainbow" streak would result filling the same pixel area as the previously discussed "white" streak. The illumination level of the scene would be reduced 16-fold and each intensity in the rainbow streak would be another $\frac{1}{16}$th that of the white streak discussed previously. If the system gain were increased 16-fold, stationary objects in the field of view would appear as though illuminated with conventional white light, but moving objects would appear as a strobed rainbow streak of lesser intensity. Thus much more information about the trajectory of the moving spot is available in the resultant TV image. Its position every 2 milliseconds is discretely available as a different color in the image.

Thus the course of certain events, trajectories and processes could be identified with greater precision than with a constant white light, using the identical TV camera and display system as normal. Indeed in such TV images with RADEL illumination, stationary objects appear as they normally do under white light illumination because at each respective pixel the 16 consecutively lit LEDs sum to white light reflecting off each stationary object. However moving objects take on a rainbow coloration effect roughly as though they had experienced chromatic aberration through a prism. Such imaging is herein called Chromatic Imaging of Subframe Trajectories, (CIST). This colorization signature signifies changes that occurred during the course of each frame. "Prismatic" separation of the colors would continue frame after frame and allow trajectory analysis and identifications in progressive scan cameras. It is also possible to use 1 millisecond or ½ millisecond LED illumination intervals and/or interlaced cameras for increased temporal resolution of moving objects. Then two or four (respectively) in-line prismatic separations of the moving object result.

In addition to identification and analysis of motion, this technique allows any events that alter "color" in a dynamic process to be discerned and identified. In particular, in addition to separating out those things in the field of view that move or change color, aesthetic video compositions can also be derived from these RADEL type illuminations in typical video systems, for example through panning or camera motion. RADEL illumination in video imaging can aesthetically enhance the image whenever the camera (or the light source) moves during the course of each frame. Using two or more spatially-separated electronically-controllable RADELs, images can be tailored to any desired degree to have "chromatic aberration type" edges, by illuminating one portion of colors from one RADEL and the other portion of colors from the other RADEL.

In effect this technique allows IDEA Probes employing CCDs to identify materials, objects, constituents and events with "comparable" facility through sequential activation of the different wavelength LEDs during the interval of any (or many) individual CCD frames. Events become articulated by the CIST type spectral decomposition that occurs in the image for anything changing coloration or relative frame position during the frame interval. Materials can thus be identified by the signature of coloration that results in the otherwise normal image when the material, or portion thereof, is perturbed. Besides motions of all types, ongoing chemical, physical or electrical reactions that change coloration, will have signatures that can be identified through pattern recognition.

For example, if one rapidly inserts a "ball point pen type IDEA probe" as described in relation to FIG. 11 (without liquid around the ball) into a container of powder or slurry material, the CIST coloration that occurs in the image as the powder is being displaced by the ball, can be used as a signature of that powder along with its more conventional spectral properties. During a priori determined frames of the image, 16 different LED colors would appear along whatever trajectories particles moved at the image surface during that frame. Particles that moved less would have those colors compressed, and those that did not move at all would have those colors coalesced into "white". Thus a signature of displacement properties by the probe of particles comprising the material is obtained in the digitized computer image upon the probe's insertion. Through pattern recognition algorithms the CIST signature can help classify into which category the material belongs. Any tip shape other than a ball could be employed.

A medical example of utilizing such CIST signatures occurs when the "ball pen" IDEA probe of FIG. 11 presses into skin displacing tissue and blood during that skin depression. If 16 different wavelengths occur in the 33 milliseconds of each frame, and say a depression of ¼" occurs during that interval, a different color excitation results during approximately each ¹⁄₆₄" of skin/tissue displacement, (roughly speaking because the probe's motion would entail acceleration). Portions of the image which changed coloration during each such ¹⁄₆₄", displacement would have respectively imaged pixels along that trajectory and "see" the different coloration as CIST signatures. Such color changes would relate to blood motion, moving skin and tissue due to normal axial motion of the probe and from sideways motion of the probe. Thus, representation of the respectively different structures, rigidity, Young's Modulus, etc. depicting arteries and veins, muscles and fat, etc. would have discernibly different temporal and spatial CIST signatures, as well as spectral signatures, all resolvable with millisecond to microsecond resolution. What has been discussed here for external skin identification is also applicable for endoscopic evaluations, at surgical cuts, for meat and food classification, indeed for all materials which flex or move from whatever impetus. Spatial separation of the different wavelengths permits "chromatic shadowing" of 3 dimensional objects for identification of basal or surface roughness type properties. CIST signatures permit identifications resulting from all types of inhomogeneous morphologies of objects and materials.

Accordingly, IDEA probes can progress through any preprogrammed or algorithmically determined sequence of stages in an identification process where not only signatures of the material's spectral properties are being evaluated; but also temporal, spatial, and motional signatures related to the material's mechanical impedance, Young's Modulus, durometer, shore hardness, granularity, grain size, vascularity, surface texture, etc. are being ascertained. Such measurements can be made highly repeatable if the position and applied pressure, force or displacement profile of the actuating probe is precisely controlled; which is relatively easy to do by numerous physical sensing means. Analogously, properties of fluids, colloids, precipitates, etc. can be determined via probe insertion or flow-by. Dust and moving particles in gas are similarly amenable to identification and analysis.

One surprising advantage as regards the identification properties of IDEA probes exemplifies in medical non-invasive diagnostics. To diagnose an illness under conventional methodology, a blood sample is taken from a patient and then through chemical and physical separations the percentage constituents are determined, for example of glucose, cholesterol, high and low density lipids, ketones, hemoglobin oxygenation, enzymes, albumen, metals, etc. This constituent profile aids a doctor towards prognosis of the malady. Accurate analysis of blood breakdown is a difficult, time consuming process usually performed by a remote laboratory using sophisticated analysis methods evolved over decades. Despite widespread use of this conventional procedure in our health care system, it is difficult to uniformly obtain precise constituent breakdowns from this procedure and then sequentially infer what is wrong from that breakdown. Errors associated with the logistics of taking and transferring blood and data increases inaccuracies. Moreover, less than optimal information is contained within the blood, whose constituents were highly dependent upon food and drug intake, exercise, sleep depravation, etc., just prior to taking the sample, as well as blood aging after sampling. Some percentage constituents, like cholesterol, are far more stable and uniform in the skin of the patient then they are in the blood.

Since the end goal of all these processes is to determine the malady, a more holistic and potentially more accurate approach is to identify in "real time" what the illness is directly from all the variables that can be measured at that time. This permits data from various symmetrical and asymmetrical parts of the body, and with immediate response to any stimulus like pressure, temperature, fatigue, etc. It further permits differential comparisons between, for example, spectral scattering signals from the vitreous humor of the eye plus that from underarm lymph nodes, compared to similar pre-trained samples of hundreds of other patients which may allow the computer algorithm to directly infer that the patient had a particular disease or abnormality. Historic diagnostic inference based on a clinician's discretion on breakdown of blood constituents have become so familiar that other methods of determining the illness are typically not considered. A powerful computer, provided with an IDEA probe (or probes), is capable of immediately analyzing whatever relevant information can be gleaned about the patient in vivo, and comparing such information correlatively with patients of known prior illness to establish directly what the patient's illness is.

Although breaking down constituents of circulatory blood samples to make malady inferences therefrom is historically familiar, it is less desirable than directly projecting the malady from non-invasively acquirable data on body tissue. Body tissue data contains considerable information about what is within the blood plus additional information not available from blood chemistry. A second IDEA probe might simultaneously examine the color of the tongue, for example. But the algorithm need not articulate each individual constituent as separately extracted, to infer what the disease is. Body tissue data can contain information that relates to blood properties, and more; though the only important end criteria would typically be what the algorithm has been trained for. Those are the primary things one wants to find out and the piecemeal intermediary constituents can obscure the end result as much as they might elucidate it. This philosophy of training to directly identify whatever classes of end results are desired, while bypassing intermediary obscurations, is a primary feature of the present invention.

Certainly for cases where IDEA probe data itself is insufficient to make an accurate identification, probe data can be used in conjunction with blood chemistry information to enhance the diagnosis. That is, the final algorithm can be devised to include all blood chemistry variables as "orthogonal information" to IDEA probe variables. The blood chemistry variables (or other variables) can be taken in to the IDEA signal processor as on-line data or inserted on a keyboard. Probe information can also be an adjunct to conventional methods. Combined data from all sources would have a higher likelihood of accurate identification than any one data source taken separately. Blood circulates over the entire body while the IDEA probe can bring data from any localized body region into the analysis since it might view any exterior surface, interior cavity, or incision if necessary. Some external maladies and processes that can be correlated and interrelated in this manner include vascular transport, venous insufficiency, burn and wound evaluation, blood constituent phenomena, skin ulceration and rashes, frostbite, drug and food sensitivities, allergies, and oxygen skin respiration.

One other feature of IDEA probes is the ability to present to any user a set of variables (OSVS) related to the identification of a specific product which can be compared to ideal variables. Thus for example, a production line examining passing tomatoes (or other fruit) can label or zone categorize each passing tomato in terms of its deviation from an ideal. The IDEA probe can be automatically made to move toward and touch each passing tomato in its process route and then label accordingly. As backup calibration there can be an optically "standardized" moderate durometer polymer having a close set of OSV's to the desired ideal variables which the probe can be made to periodically contact. Thus any long term drift of the LEDs, detectors, epoxy surfaces or geometry can be automatically "zeroed out" after each such calibration. The stability of the standard becomes the standard of the system.

If consecutive LED excitation cycles occur at multiples of the power line frequency [with possible oversampling of each respective multiplexed pixel channel] full frames can result every 30th (or 25th) of a second and N color video (plus ambient optional) is attainable in compatible TV format. This reduces optical background noise at power line frequency multiples and the signal can be replayed on a conventional TV (or a synchronized computer monitor display). Because N may be as high as 15 to 30 (with the one off condition being deleted in replay) this has utility far exceeding RGB video for the visual identification of objects, materials, properties or scenes which are either stationary or change with time. False color can be used to represent the infrared. When cooled with CCD and CID devices those N wavelengths can cover the spectral band from 400 nm to 5000 nm increasing the joint combination of wavelength informational permutations of N=3 for three RGB wavelengths, compared to N=15 wavelengths to be approximately 6000 to 1. Because of the excellent long term output stability of LEDs, the illumination flux is highly repeatable allowing for example, the imaging system with a stable CCD to be used spectroradiometrically. The absolute quantitative characterization of scattering material is feasible.

Figure 12:
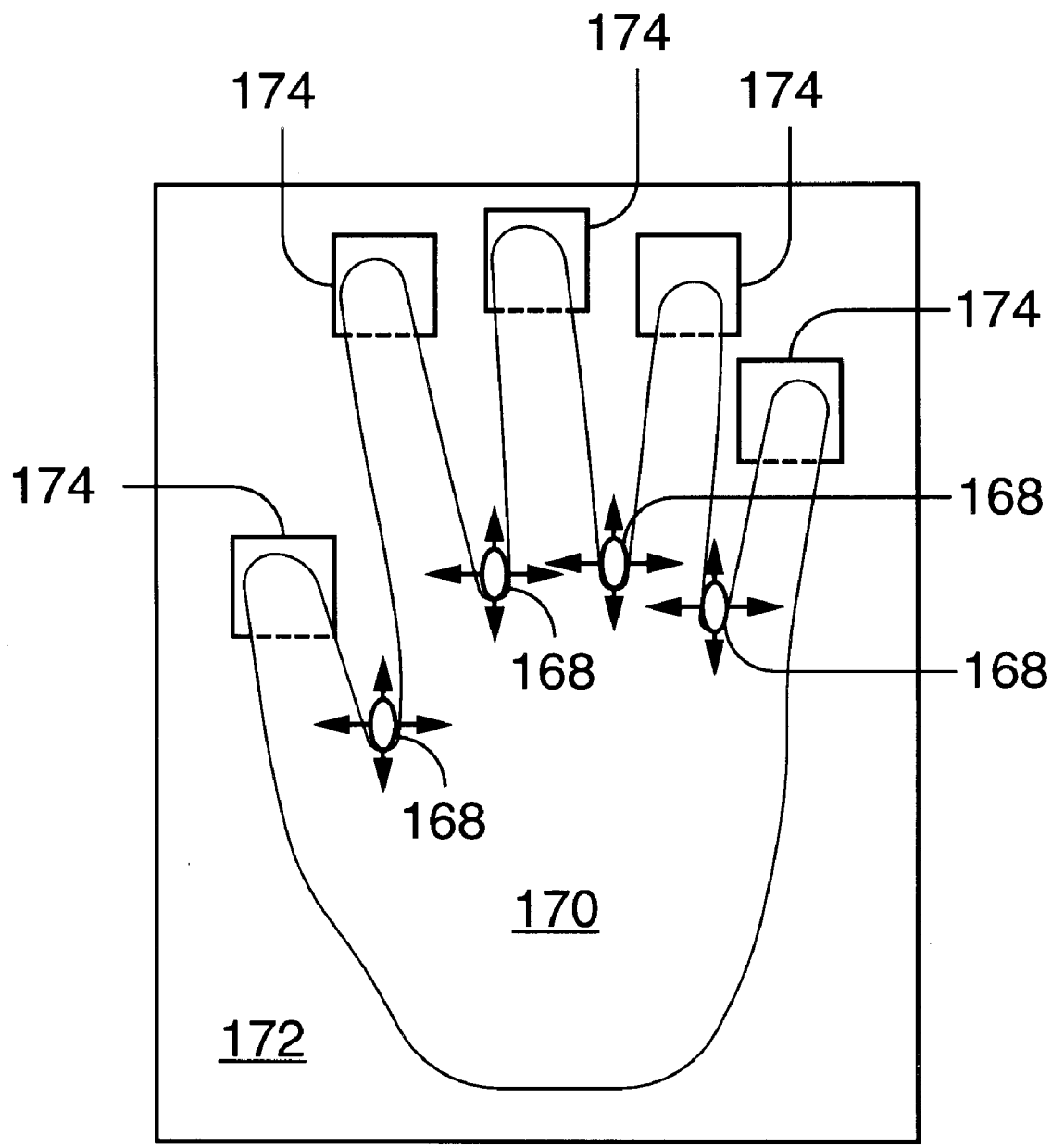
FIG. 12 illustrates an collection of IDEA probes used for rapid identification of human individuals.

FIG. 12 illustrates a useful application of the IDEA probe for rapid identification of human individuals. Four separate linear assemblies 168 can be employed in one identifier system, where each is positioned to fit between consecutive pairs of the five fingers of a hand 170, as shown. Because tissue between the fingers does not often interact with foreign objects it presents a preferable and convenient region of the body to use for optical subcutaneous identifications. The four IDEA probe assemblies 168 are each separately spring loaded toward the palm along a track within a flat plate 172 onto which the hand is placed and moved forward (upward) against the springs. The tissue between each pair of fingers pushes up on the IDEA identifier. Although various methods are available to sense and restore probe assembly positions, a linear displacement potentiometer can be used to register the extent of motion of each assembly. These displacement sensors are used in much the same way as those described in relation to FIG. 9. In a preferred embodiment, each assembly on each track can move vertically about 2 in. and also sideways (left or right) about 0.35 in. to accommodate the variable spacing between fingers for different individuals. The spring loading positions of each assembly is in the approximate center of that 0.35 in. and when the hand stops an X direction linear displacement potentiometer registers the final X position of each IDEA array and a Y direction linear-potentiometer registers the final Y position.

Each linear IDEA assembly need not protrude perfectly normal to the flat plate but may be tilted downward above the plate the average slope of a human hand or about 15° off normal. The assumed N=15 LEDs spaced on 0.025 inch centers comprise a 0.025×15=0.375 in. active optical region beginning about 0.125 in. above the flat surface. The hand is placed on the plate with protruding assemblies between each finger and then the hand is moved forward in one motion so as to engage and displace all assemblies upward. The fingers are then moved together to a halt surrounding each assembly. About one half second after the signal variables stop changing, a reading of all OSVs can be taken and analyzed. Discriminators for the algorithm comprise the relative final positions amongst the assemblies (each in X and Y relative to the others derived from the potentiometers) and the optical throughputs of the RADEL/PIXEL arrays (nominally 4 MN=4×15×4=240 throughputs).

A simple example of an identification process as discussed in this invention is articulated below to exemplify how one discrimination algorithm works. Numerous other algorithmic methods may also be used, and typically more esoteric than the description here. Assume each linear track is 1.5 in. long in the Y direction and for simplicity of discussion can be readily resolved into ten positions of 0.15 in. each. Actually, electrical resolution from a potentiometer could yield perhaps tenfold better resolution. Assume a linear X-direction motion of 0.5 in. is possible and the X direction is resolvable into 4 parts of 0.175 in. each, again quantizing the motion into large increments for simplicity. Eight different mechanical readings result; four vertical and four horizontal but only 3 in each orthogonal direction are relative to the remaining one. Therefore, relative to one Y displacement there can be 10×10×10=1000 possible increments of the other positions, or 5×5×5=125 possible increments if one increment of uncertainty is allowed. For the X displacement there would be 4×4×4=64 possible increments or 2×2×2=8 possible increments of position if one increment of uncertainly is allowed. For the poorer case, the combined discrimination of both X and Y directions would entail 125×8=1000 combinations for the mechanical hand-sizing part of the identification. This would be compounded by the RADEL/PIXEL OSV part of the identification which can be envisioned to permit however many increments of value upon each of the 240 additional variables. It is notable that the number of combinations becomes enormous and the matrix of values for any specific hand is not likely to match closely the matrix for another arbitrary hand.

The description here has been highly simplified by quantifying the increments into coarse values for reasons of explanation. More realistically we now consider each potentiometer output as resolvable to one part in 100 (or greater). Relative to the final position of one assembly a value from 1 to 100 could associate with each of the other final resting positions in a training set to calibrate a specific person's hand. Plausibly there would be several consecutive training measurements to form a set and the mean value of all these final resting positions would constitute the retrievable value in memory needed when checking to see if an individual being tested subsequently matches his/her training set. The standard deviation of the training readings might also be recorded to be used as weighing factor in how "sloppy" (fuzzy) the match for that individual need be.

The same individual being later checked is unlikely to have within one increment of the mean value for the 100 or more possible increments for each mechanical variable. But the difference he/she registers from the mean is a defined number and the sum of the squares of all differences (mean square difference) from their respective means provides for example, one criteria of match between the individual being tested and the training set. The smaller the sum of the squares of all differences, the more likely the individual matches the training set. Beyond some predetermined threshold, perhaps influenced by the standard deviations, the match is considered invalid or a criteria of mismatch is derived. If the computer is checking to see if this specific person created the pretrained set designated John Doe, it simply compares the sum of the squares difference between that person's reading and the trained mean values for John Doe, (including weighing for standard deviations, etc.). If the computer is not programmed in advance for a specific individual, all it can do is compare that individual's values with the mean values for all persons in its pretrained library and conclude who in the library is closest, next closest, etc. to the tested individual (by least mean squares difference measure) and produce a number indicating how close the match is to that library member. If not very close the individual might be required to disclose a Personal Identification Number. If there are a large number of permitted persons in the allowed total library set (say thousands) or if the match is marginal a PIN number might be required.

The PIN is easily implemented for example by the sequential pressure of each finger tip after the hand motion stops on a collection of membrane switches 174 at the upper end of each track.. If only four of the five fingers actuate such a "combinative lock" sequence of four consecutive switch depressions, this would constitute a further discrimination of (one part in four)$^4$=($\frac{1}{4}$)$^4$=1 part in 256. For actuating each of the switches on five fingers, ($\frac{1}{5}$)$^5$ yields a discrimination factor of 1 in 3125.

In analogy to this electromechanical description of discrimination, all of the 240 optical throughput values from the LED/detector assemblies 168 will yield a mean square difference (msd) between each respective pretrained value. The sum of these squares difference, along with the mechanically derived sum of the squares difference (appropriately weighed) provides the overall match criteria of identification. It becomes apparent that it would be very difficult to fool the system with regard to correctly identifying individuals. The speed of a modern personal computer or a DSP enables completion of the computation in less than one second. It should be noted that in addition to a least squares analysis as discussed, the computer program would likely algorithmically derive feature sets from the training data that aided discrimination of each respective individual. Each person's feature set would be used in the discrimination algorithm along with the sum of squares comparison described here primarily for descriptive simplicity. A feature set constitutes an extraction from among the OSV for each person's training data that is statistically "most different" from all the other persons trained for in regard to discrimination needs. It generally entails those specific correlation's amongst an individual's OSVs that are not highly representative of the remaining individuals in the training set. Any of the prior mentioned algorithmic procedures could alternatively be used. The method described was exemplary for reasons of simplicity.

The delineation above was based on mechanical aspects of the algorithm for descriptive visualization purposes. In actuality, from the optical variables portrayed, the computer could register all 240 readings in 2.4 milliseconds or less with 16 bit accuracy (one part in 65,536), assuming low cost 10 microsecond A/D conversion times. Similarly increased resolution would be pragmatically appropriate for the potentiometers which sense the mechanical components. As described, small mismatches in the resultant sum of the squares would not likely be the factor limiting long term precision of identification, but rather overall repeatability due to mechanical repositioning and biological tissue changes over time. What was discussed above for a flat plate with IDEA protrusions is also applicable for a handle with analogous movable protrusions; say a gun or carshift handle. Only the pretrained hand as identified by the algorithm could actuate that handle. Thus, automatic safe handles for apparatus are feasible utilizing IDEA probes.

In fabricating a circular ring or linear embodiment of LEDs it is often desirable to actuate several LEDs connected in series electrically, (generally of related or similar wavelengths). This occurs for example when each of the N different wavelengths is compounded of S discrete same wavelength LED die symmetrically located around a circular perimeter. That is, for example, the S discrete die of one wavelength all actuate together as radial spokes of a wheel to achieve uniform "ring" illumination of that wavelength derived from 360°/S positions. For the second of the N wavelengths there would then be S more die of wavelength 2 incremented 360°/N(S) from the first wavelength die. Actually S at wavelength 2 might sometimes differ from S at wavelength 1, to compensate for differences in electron/photon efficiencies or bandgap voltages between N(1) and N(2). This interspersed incrementing continues N-fold times for all the wavelengths so that the NS total die are all equally spaced around the perimeter every 360°/N(S) degrees and all die of the same wavelength are equally spaced every 360°/N degrees. (For example, the embodiment of FIG. 5 may have S=12 so that each face of the 12-sided polygon has a set of N LEDs which are similar to those on every other face.) By connecting the same S wavelength die in series a single current source driver requiring slightly more than S times the LED bandgap voltage can suffice to drive the S LEDs simultaneously. This simplifies the drive circuitry for the more uniformly illuminated "ring lights" of each wavelength.

To give a specific numerical example suppose N=16 and S=4 (see FIG. 4B), with 16×4=64 LEDs in that specific case. Then each of the same wavelength LEDs will comprise 4 spokes, 360/4=90 degrees apart and there will be 16 such different wavelength integrated 4 spoke arrays so that each LED has an angular separation of 90/16=5.625 degrees. To achieve this configuration there must be 64 die attachments on a substrate and 64 bondwires and bonding pads. Electromagnetic or optical coupling between the LED drive and the detection system should be virtually zero in the absence of a sample which requirement further restricts the component and lead positions and grounding circuit topology. Peak LED on currents can be 100 mA while the equivalent noise current of the detector can be in the picoamp region. For optimum performance almost 8 or 9 orders of magnitude of electromagnetic and optical isolation are required between the LED drive system and the detector system in close proximity. Moreover, a good heat sink is desired otherwise the components may overheat, or be at different temperatures. Heat sink efficacy effectively limits the maximum drive current to the LEDs. To fabricate a generalized configuration the combination of all these considerations imposes the following desired nontrivial inferences on the printed circuit board and circuit layout.

1) Components or circuit wiring leads should be avoided on the inner radial side of the LEDs, the region where the radiation will be used.

2) Space for a ground plane and heat sink should be available on the opposite side of the LEDs, their bond pads, and associated wiring.

3) The bond leads and board pads should be as close to the LEDs as feasible such that an angular reflective surface over them can deflect radiation from the undesired LEDs radiation direction to a desired direction.

4) Either n or p type die shall be capable of being driven from a unidirectional source in a multiplexer connected to a common current source.

5) The LEDs should be spaced as closely as fabrication allows, PCB lead wires should not progress between LEDs.

6) It is desirable to be able to configure N wavelengths comprised of Q drive circuits each of S LEDs in series on the same PC board (or at least using the same LED interconnection region). For NQS total die on the same PC board, Q, N and S should be changeable at the time of insertion for any value of N up to a maximum. Wires and terminations to the series connected LEDs should be easily accessible to the driver circuitry. In this case, for example, N can be 16 with Q=1, or N=8 with Q=2, which would allow two shadow directions for each of the 8 wavelengths. Or, N can be 8 with S=8 and Q=1. This significantly reduces the number of PC boards needed and the physical, thermal, optical environment of components and elements becomes ostensibly the same for all systems configured with these differing values of N and S. Compensations and calibrations in manufacture can thus be more precise with less effort. Custom designs on the same PC board also become feasible. 7) The arrangement should allow for maximum light output either in an annulus normal to the top surface of the die, or by using a separate annular reflective ring of necessary contour, flooding the central circular region with radiation.

8) There should be facility to accommodate LED drive components such as analog switches or multiplexers and current supplies that may be pulsed (either in die or from a package), reasonably close to but not directly in back of the LED die and lead-bond area. Preferably, it should be possible to place them on either side of the board leaving the other side available for the detector system. The circuit loops from current supplies through multiplexers, LEDs and return should generally entail as small a loop as feasible and be shielded so as to emit the least amount of electromagnetic interference coupling (EMI). No single drive current loop should radiate significantly different EMI then any of the other loops. What little EMI emission may exist should be temporal periodic with each consecutive LED on intervals, so that any unwanted coupling could not potentially predistort one wavelength contributions relative to the others.

9) Costs in moderate to large volume should be reasonable, relative to achieving the desired functionality. Repeatability should be high and shorted or open leads should be rare. Die attaching and lead bonding pairs should be totally selectable at time of die attachment and lead bond assembly both by LED placement and drive current sequence. Any size LED die up to about 0.20 in. square should be adequate.

For heat sinking a heavy copper annulus or aluminum would usually be bonded to the ground plane copper on the rear of the thin PC board. A conical reflective ring, usually metallic, would cover the die and bond wire region while being flush with the PC board for a segment of the radial traces as indicated.

The embodiments discussed here are exemplary of a generic method to configure variable sized LEDs of differing wavelengths N in a uniform topology to attain "standardized" regions of spectroradiometric radiation (and detection). Additional applications of computer driven Radel arrays include generating in real time an arbitrary spectral density distribution of optical radiation in response to control commands. Computer signals can activate every LED of a Radel array in any parallel or serial sequence combination thereby dynamically synthesizing a desired spectral, temporal and spatial density in response to prevailing real time circumstances encountered by the computer. Examples include:

a) As different biota, cells, or chemicals pass within the field of view of a microscope and are identified by a pattern recognition algorithm, an extended algorithm can decide what custom spectral radiation to illuminate each distinct entity with in order to cause a desired effect or to increase the identification accuracy. The light might activate one type biota one way, a second another way, and a third another way, etc.

b) By various gene altering techniques it is possible to hybridize plants and biota so that their seeds, eggs, or spores will not germinate unless sequentially illuminated by the proper sequence of illumination. Such "proper" illumination can be derived from a RADEL array for each different type biota encountered in real time.

c) Encrypting optical data signals by spectrally switching wavelengths in accord with some predetermined code.

d) Photochromic materials can be studied and actuated under computer control by RADEL arrays so as to make them optically code-sensitive even if they are not normally so.

e) Dynamic compensation or control for changing ambient illumination in video, movie or still photography to achieve a desired spectral rendition, or to articulate sub-frame motion within the field-of-view.

f) For measuring optical system response times to different spectral compositions; for example, for the iris of the eye and for insect, mammalian or machine responses to spectral distribution changes.

g) For modulating spectral distributions in real time in accord with a desired function, namely optical, discrete FM and AM. These can be used in measuring optical modulation products in non-linear interactions.

In summary, the following features are incorporated into numerous applications of this invention.

1. Spectrometer IDEA probes are based on digitally controllable semiconductor or polymer luminescence.

2. Since N wavelengths can be actuated independently or simultaneously the excitation energy can have virtually any spectral envelope within constraints of the N possible emissions.

3. Configurations are computer controllable in "real time" to digitally change wavelength, illumination sequence, multiple wavelength overlap, on-time of each wavelength, shadowing, analog number of photons/sec, spatial position of the illuminating source; and all in response to measured characteristics of the sample. The test program can be "interactive" dependent upon what is sensed in the testing.

4. Irradiations are roughly linear with drive current and compatible with analysis methods based upon the density of states of the test material.

5. Absorption measurements of properties of the test materials are amenable to non-linear spectroscopy methods that can provide new spectrometric signatures. One may separately ascertain the absorption coefficients and elastic scattering coefficients through such non-linear spectroscopy.

6. Relatively high spectral densities are available from the emission LED die which can be placed very close to the test sample. A large dynamic range of intensities are applicable at most wavelengths.

7. Because wafers of many different alloys are necessary in making die of respectively different wavelengths, substrate assemblies composed of such different die need to be used in many different applications to make such applications economically viable. This generic specialization of Radel arrays will still remain applicable even when single chip ASIC multiwavelength emitters are used in IDEA probes.

8. IDEA probes can be useful for identification, classification, sorting, property analysis, modeling or differential comparisons of materials or objects as the desired case may be. They can be applied to solids, liquids, powders or gases.

9. Using IDEA probes it is possible to very rapidly measure spectral, spatial and temporal optical properties of materials.

10. Because the impinging radiation source is nearly Lambertian, configuration set-ups have less geometry dependence for scattering materials than with optical beams. It also makes propagation of the radiation subject to diffusion equation analysis, rather than being indeterminate.

11. Surface and bulk properties can be separately measured and characterized even in highly turbid or quasi-opaque materials. Surface anomalies of the material can be circumvented, at least in part, in the measurement result.

12. IDEA probes are directly usable in room light by methods of subtracting out the background illumination. In artificially illuminated areas there is typically significant 120 cycle (and higher in multiples of 60) optical fluctuations from incandescent/fluorescent lamp variations. This background optical "noise" is difficult to cancel out for other than fast strobed spectral sources like LEDs which can have microsecond responses.

13. IDEA probes can be very small, and portable, from virtually toothpick to pencil size, having no moving parts, require very little power, and when subassemblies are manufactured for numerous applications, can be relatively low cost. They are ideal for hand held instruments/systems.

14. A large spectral range of excitations are feasible, currently from 400 nm to 4700 nm as commercially available LED die. Using silicon detectors 400 nm to 1000 nm can be sensed and zinc sulfide or other IR detector materials, cooled or uncooled, can be utilized at longer wavelengths.

15. CCD arrays and RADEL arrays as incorporated in IDEA probes constitute input/output peripherals of contemporary computers and are useful to let the computer interrogate the outside world via spectral photons. This provides very useful acquisition-at-a-distance information to a computational machine.

16. Various feasible computer algorithms and hardware drive/sensing configurations are feasible that can be dynamically (interactively) altered, even during the course of measurement. Sequential algorithms can be enacted for redundancy in discriminations when ambiguous identifications result from insufficient algorithmic conclusions.

17. Four to ten probes can be on the fingertips of a glove so that a person or a robot picking tomatoes (or something similar) can tell instantly if they are ripe before picking.

18. Hand identification of an individual can be achieved from any functional handle or plate having IDEA probe protrusions radiating angularly from a gun type handle being displaced between fingers. The hand identification properties can be used to identify the users of various hand held devices such as telephones, tools, door knobs, car door handles, shifts, etc.

19. Relative calibration for checking throughput of IDEA probes is readily feasible with a clear thin spacer sheet sandwiched to a broadband "white" optical reflector.

20. IDEA probes can be amplitude calibrated at any time by simply placing them against a reflector or standard optical scattering polymer of low durometer and having the computer monitor throughputs in calibration position.

21. Substrate PC boards can have a generalized layout accommodating different N and Q numbers, and providing one heat sink assembly for all emitters and detectors.

22. Spectral bi-directional sensing (in the full duplex sense) communication are feasible between probes in different locations through multiplexing methods. Two or more probes achieve more than the sum of their separate parts.

23. The use of IDEA probes in transdermal processes enables the multi-dimensional sensing of coloration that can be associated with transport. This feature of providing information that contains many degrees of freedom associated with a process, rather than one or a few degrees, is analogouly applicable to a wide range of medical and industrial processes. Conversion of a variable into a spectral evaluation generally provides multi-dimensional vector information, rather than scalar information, about the process.

RADELS and IDEA probes represent a form of Digital Spectroscopy which, when computer activated for material identification, can be superior to analog continuous-spectra spectroscopy because, among other reasons:

1) The spectral signal from any monochrometer actually derives from the convolution of all wavelengths within the passband. Signals do not derive from a truly single wavelength response, but from an integration of many close wavelength responses. When operating with a computer the signal processor must subsequently quantize (lump) these responses into discrete digital values for its utilization. The computer is a digital machine and must function via digital data. It is not highly compatible with monochromatized signals.

2) The ability to rapidly overlap a collection of LED wavelengths in sub-100-microsecond intervals implies that virtually no unwanted intervening changes in the system can occur within such short intervals. Therefore, sequential differential comparisons made within those intervals can be highly precise because only the illumination level changes, nothing else can drift between measurements. Conventional spectrometers cannot change their spectral envelope rapidly and certainly not while containing arbitrarily programmable rejected-wavelengths within the passband.

3) LED/Detector throughput arrays have good signal compatibility with genetic algorithms, principal component algorithms, neural networks, etc. for operation into computer, microcontrollers, DSP's etc.

4) With say N=15 different independently applicable wavelengths there can be up to $2^{15}$=32,768 resultant variables each having a large dynamic range. This represents a tremendous amount of rapidly-acquirable computer-compatible data about the test object, far more than obtainable with a scanning monochrometer. A change represented by a small shift in peak monochrometer wavelength occurring in say 10 microseconds generally constitutes less of a change than a gross alteration in the excitation's spectral envelope. Often, identification ability per unit time represents the figure of merit of a spectral system and particularly so for dynamic industrial/medical processes. Such systems usually change slightly with ongoing production processes or with each heartbeat or breath.

5) Probing from one state of excitation to a closely adjacent state via the continuous change of a monochrometer output is not as desirable as discretely switching the state of excitation in terms of determining: a) The material's transient effects, e.g. due to non-zero lifetimes, b) Thermal effects from different absorbed energies or electrical dissipation.

6) Techniques are available to create slight shifts in the peak output wavelengths of LEDs; for example, by allowing the die to heat by driving it at a significantly higher-than-normal current. The skirts of the LED output then permit some examination of (anticipated) narrow-spectral lines, much as is achieved with scanning monochrometers. Wavelengths between the lines need not be comparably scanned thereby deleting data which is less useful. The resolution obtainable from LEDs in this manner is generally less than obtainable than with a quality monochrometer system but can still suffice for many applications. Very small controlled wavelength shifts can be achieved in the manner, which shifts can be near narrow absorption lines of test materials.

7) Combinations of the above features, in addition to other features described in the specification, can be included in many IDEA probe embodiments.

The above detailed description of various embodiments of the invention contains many specifics for the purposes of illustration and enablement. Nevertheless, as the wide variation in embodiments demonstrates, the invention should not be determined by the specifics in these embodiments, but by the following claims and their legal equivalents.

What is claimed is:

1. A device comprising:
   a collection of light sources which emit light over a collection of corresponding source spectral distributions toward an object to produce scattered light, wherein the number of light sources is at least five and the corresponding source spectral distributions comprise at least four distinct spectral distributions;
   a light source driver which independently controls the emission of light from each of the light sources;
   a collection of optical detectors which detect portions of the scattered light and produce signals representative of the detected light, wherein the number of optical detectors is one or more; and
   a signal processor which receives the signals from the collection of optical detectors and compares the signals with a reference characteristic of a reference object, wherein the signal processor is previously trained by training signals associated with the reference object.

2. The device of claim 1 wherein the signal processor compares the signals with a plurality of reference characteristics of a plurality of reference objects, wherein the signal processor is previously trained by training signals associated with the plurality of reference objects.

3. The device of claim 1 wherein the training signals derive from the optical detectors.

4. The device of claim 1 wherein at least two of the source wavelenghths are identical to each other.

5. The device of claim 1 wherein the distinct source spectral distributions differ by at least 0.5 nanometers.

6. The device of claim 1 further comprising an optical barrier which prevents light from traveling directly from the light sources to the optical detectors.

7. The device of claim 1 wherein the light sources have a predetermined spatial arrangement and wherein the light source driver actuates the light sources in a predetermined temporal sequence.

8. The device of claim 1 wherein the light sources and optical detectors are fixed on a hand glove.

9. The device of claim 1 wherein the light sources and optical detectors are fixed on a collection of independently movable members.

10. The device of claim 1 wherein the scattered light comprises fluorescent light, transmitted light, or phosphorescent light from the object.

11. The device of claim 1 wherein the scattered light comprises bulk scattered retro-reflection from the object.

12. The device of claim 1 wherein the signal processor determines from the signals a thermal, temperature, mechanical, stress, strain, weight, viscosity, turbidity density, shadowing, luminescence lifetime, electrokinetic, notional, spectral, or temporal property of the object.

13. The device of claim 1 wherein the signal processor determines from the signals a nonlinear property of the object.

14. The device of claim 13 wherein the nonlinear property derives from transitions between excitable states of the object.

15. The device of claim 1 wherein the light sources are semiconductor or polymer luminescence devices, e.g. light emitting diodes or laser diodes.

16. The device of claim 1 further comprising an optical element positioned in a path of the light emitted from one or more of the light sources.

17. The device of claim 16 wherein the optical element is a clear refractive material, prism, lens, reflector, filter, or grating.

18. The device of claim 1 further comprising an optical element positioned in a path of the light detected by one or more of the optical detectors.

19. The device of claim 18 wherein the optical element is a clear refractive material, prism, lens, reflector, filter, or grating.

20. The device of claim 1 wherein the optical detectors are charge coupled devices, photovoltaic detectors, PIN detectors, photodiodes, charge injection devices, image intensifiers, photoconductor detectors, avalanche detectors, or photomultipliers.

21. The device of claim 1 wherein the optical detectors are charge coupled devices, a CID, CMOS imaging chip, or a 2-dimensional detector array, wherein the signals representative of the detected light are divided into temporal image frames, and wherein the light source driver activates a predetermined sequence of the light sources within each of the image frames.

22. The device of claim 21 wherein the light source driver controls the light sources such that a predetermined sequence of light sources is activated in consecutive image frames.

23. The device of claim 1 wherein the spectral distributions of the light emitted from the light sources are primarily within the range of 200 nm to 5000 nm.

24. The device of claim 1 wherein the spectral distributions of the light emitted from the light sources are primarily within the range of 200 nm to 2 cm, whereby the device may be used to identify properties of the object cooled below 72 K.

25. The device of claim 1 wherein the light source driver controls the light sources such that at least two light sources produce light pulses having envelopes that partially overlap in sub-100 millisecond time intervals, thereby permitting the measurement of coupling by the object between different spectral distributions.

26. The device of claim 1 wherein the light source driver modulates the light emitted from the light sources in both an analog and digital manner.

27. The device of claim 26 wherein the light source driver modulates the spectral distribution of light emitted from at least one of the light sources.

28. The device of claim 1 wherein the number of light sources is at least ten.

29. The device of claim 1 further comprising an optical shroud surrounding the optical detectors, whereby the amount of ambient light reaching the detectors is reduced.

30. The device of claim 1 wherein each optical detector comprises an A/D converter which converts the signals representative of the detected light from analog to digital.

31. The device of claim 30 wherein the A/D converter has at least 16 bit resolution.

32. The device of claim 1 wherein the light sources and the optical detectors surround the object.

33. The device of claim 32 wherein the object is a solid, liquid, powder, gas, or slurry.

34. The device of claim 1 further comprising at least one lens which focuses the scattered light upon a planar arrangement of the optical detectors.

35. The device of claim 1 wherein the signal processor receives a supplementary temperature, acoustic, electromagnetic, capacative, magnetic, electrokinetic, airborne gas, vibration, motion, pressure, force, ultrasonic, or electrical signal from the object, and wherein the training signals are further associated with corresponding supplementary signals of the reference object.

36. The device of claim 1 wherein the signal processor is programmed to receive a distance signal representing a distance from a surface of the object to the collection of detectors, and wherein the training signals are further associated with distances from the reference object.

37. The device of claim 1 wherein the signal processor comprises a neural net, a DPS, a general purpose microprocessor, or a human interface.

38. The device of claim 1 wherein the signal processor determines an elastic back-scattering property of the object, a fluorescence property of the object, or a phosphorescence property of the object.

39. A method for identifying properties of a material object, the method comprising:
independently controlling the emission of light having distinct spectral distributions from at least five distinct light sources;
scattering from the object the emitted light;
detecting the scattered light with one or more optical detectors that produce signals representative of the detected light, wherein the signals comprise an optical interaction signature correlated with a density of states property of the material; and
associating the signals with reference signals of a reference object.

40. The method of claim 39 further comprising independently controlling the emission of light from the light sources so that a predetermined sequence of distinct spectral distribution pulses is emitted during a repeating time interval, and wherein the signals representative of the detected light are produced once during each of the time intervals.

41. The method of claim 39 wherein the controlling of the emission of light comprises controlling the light sources such that at least two light sources produce light pulses having envelopes that partially overlap in sub-100 millisecond time intervals.

42. The method of claim 39 further comprising measuring a variable associated with a physical state of the object and associating the variable with a similar variable of the reference object.

43. The method of claim 42 wherein the variable is relative velocity, relative position, acceleration, space-time coordinates, strain, stress, emitted airborne gasses, surface ions, humidity, inertial forces, dynamic forces, magnetic forces, capacitance, electrokinetic effects, flexability, temperature, pressure, electromagnetic field strength, electrical resistance, voltage, or current.

44. The method of claim 39 wherein the light sources and the optical detectors surround the object.

45. The method of claim 39 wherein the associating step comprises a multivariate analysis.

46. The method of claim 39 wherein the associating comprises comparing the signals with reference signals of a plurality of reference objects.

47. The method of claim 39 wherein the associating comprises comparing the signals with past signals associated with a plurality of reference objects.

48. The method of claim 39 further comprising changing an optical path length between the light sources and the object, wherein the associating step comprises analysis of radiation signals detected at different path lengths.

49. A method for identifying properties of a material object, the method comprising:
generating light using four or more independently controlled light sources having three or more distinct spectral distributions;
irradiating the object with the light;
detecting from the object radiation signals representative of a response of the object to the light; and
identifying a property of the object by analysis of the radiation signals, wherein the identifying step comprises comparing the radiation signals to reference data representing properties of a reference object, wherein the reference data is derived from a training procedure.

50. The method of claim 49 wherein the light sources are semiconductor junction emission devices, such as LEDs, laser diodes, or polymers.

51. The method of claim 49 wherein the light sources are arranged in a dense array.

52. The method of claim 49 wherein the detecting step comprises using a dense detector array.

53. The method of claim 49 further comprising changing an optical path length between the light sources and the object, wherein the identifying step comprises analysis of radiation signals detected at different path lengths.

54. The method of claim 53 wherein the optical path length changes by less than 10 cm.

55. The method of claim 49 wherein the identifying step comprises a multivariate analysis.

56. The method of claim 49 wherein the identifying step comprises comparing radiation signals detected at a time $t_2$ with the sum of radiation signals detected at a time $t_1$ and radiation signals detected at a time $t_3$.

57. The method of claim 56 wherein at time $t_2$ a first light source and a second light source are simultaneously generating light, at time $t_1$ the first light source is generating light and the second light source is not generating light, and at time $t_3$ the first light source is not generating light and the second light source is generating light.

58. A method for identifying properties of a material object, the method comprising:
- generating light using three or more light sources having three or more distinct spectral distributions, wherein the light sources are positioned on a first side of an optical barrier;
- irradiating the object with the light;
- changing the relative positions of the optical barrier and the object;
- determining a plurality of distances between the optical barrier and the object;
- detecting from the object radiation signals representative of a response of the object to the light at each of the plurality of distances, wherein the detecting uses optical detectors positioned on a second side of the optical barrier; and
- associating a property of the object with a reference property of a reference object using multivariate analysis of the radiation signals.

59. The method of claim 58 wherein the identifying step comprises comparing the radiation signals to reference data representing properties of a reference object.

60. The method of claim 58 wherein the plurality of distances comprise two extreme distances differing from each other by at least 2 cm.

61. The method of claim 58 wherein the plurality of distances comprise a distance less than 2 cm.

62. The method of claim 61 wherein the plurality of distances comprise a distance less than 1 mm.

63. The method of claim 58 wherein the generating of light comprises controlling the light sources such that at least two light sources produce light pulses having envelopes that partially overlap in sub-100 millisecond time intervals.

64. The method of claim 58 further comprising measuring a variable associated with a physical state of the object and wherein the associating step comprises comparing the variable with a similar variable of the reference object.

65. The method of claim 64 wherein the variable is relative velocity, relative position, acceleration, space-time coordinates, strain, stress, emitted airborne gasses, surface ions, humidity, inertial forces, dynamic forces, magnetic forces, temperature, pressure, electromagnetic field strength, electrical resistance, voltage, or current.

66. A method of photometric analysis of a material object, the method comprising the steps of:
- irradiating the object with four or more light sources having substantially distinct wavelength envelopes, wherein the irradiating comprises activating the light sources in a sequence of distinct combinations, wherein the distinct combinations have an average temporal separation of less than 100 ms;
- detecting radiation from the object with a collection of spatially distributed light detectors to produce detected signals;
- synchronizing the detected signals with the activation of the sequence of distinct combinations of the light sources to produce associated combinations of detected signals; and
- analyzing the combinations of detected signals to determine a physical property of the object.

* * * * *